US009730994B2

(12) United States Patent
Pietrobon et al.

(10) Patent No.: US 9,730,994 B2
(45) Date of Patent: Aug. 15, 2017

(54) COMPOSITIONS AND METHODS FOR IMMUNIZING AGAINST C. DIFFICILE

(71) Applicant: Sanofi Pasteur, Inc., Swiftwater, PA (US)

(72) Inventors: Patricia Pietrobon, Swiftwater, PA (US); Ginamarie Foglia, Swiftwater, PA (US); Guy De Bruyn, Swiftwater, PA (US); Sanjay Gurunathan, Swiftwater, PA (US)

(73) Assignee: SANOFI PASTEUR, INC., Swiftwater, PA (US)

( * ) Notice: Subject to any disclaimer, the term of this patent is extended or adjusted under 35 U.S.C. 154(b) by 0 days.

(21) Appl. No.: 14/897,870

(22) PCT Filed: Jun. 13, 2014

(86) PCT No.: PCT/US2014/042298
§ 371 (c)(1),
(2) Date: Dec. 11, 2015

(87) PCT Pub. No.: WO2014/201346
PCT Pub. Date: Dec. 18, 2014

(65) Prior Publication Data
US 2016/0120968 A1    May 5, 2016

Related U.S. Application Data

(60) Provisional application No. 61/835,246, filed on Jun. 14, 2013.

(51) Int. Cl.
*A61K 39/08* (2006.01)
*A61K 39/00* (2006.01)

(52) U.S. Cl.
CPC ........ *A61K 39/08* (2013.01); *A61K 2039/545* (2013.01); *A61K 2039/55* (2013.01); *A61K 2039/55511* (2013.01)

(58) Field of Classification Search
None
See application file for complete search history.

(56) References Cited

U.S. PATENT DOCUMENTS

| 6,214,341 | B1 | 4/2001 | Thomas, Jr. et al. |
| 6,680,168 | B2 | 1/2004 | Thomas, Jr. et al. |
| 6,969,520 | B2 | 11/2005 | Thomas, Jr. et al. |
| 2006/0029608 | A1 | 2/2006 | Thomas, Jr. et al. |
| 2007/0231336 | A1 | 10/2007 | Thomas, Jr. et al. |
| 2011/0045025 | A1 | 2/2011 | Middaugh et al. |
| 2013/0004561 | A1 | 1/2013 | Shone et al. |
| 2013/0177592 | A1 | 7/2013 | Thomas, Jr. et al. |
| 2015/0044250 | A1 | 2/2015 | Heinrichs et al. |
| 2015/0093389 | A1 | 4/2015 | Shone et al. |

FOREIGN PATENT DOCUMENTS

| WO | 2014/144567 | 9/2014 |
| WO | 2014/144594 | 9/2014 |

OTHER PUBLICATIONS

Ananthakrishnan, Ashwin N., "Clostridium difficile infection: epidemiology, risk factors and management", Nature reviews Gastroenterology & Hepatology, vol. 8, No. 1, Jan. 2011, pp. 17-26.
Anosova et al., "Systemic antibody responses induced by a two-component Clostridium difficile toxoid vaccine protect against C. difficile-associated disease in hamsters", Journal of Medical Microbiology, vol. 62, No. 9, Sep. 2013, pp. 1394-1404.
Aslam et al., "Treatment of Clostridium difficile-associated disease: old therapies and new strategies", The Lancet Infectious Diseases, vol. 5, No. 9, Sep. 2005, pp. 549-557.
Chang et al., "Onset of symptoms and time to diagnosis of Clostridium difficile-associated disease following discharge from an acute care hospital", Infection Control and Hospital Epidemiology, vol. 28, No. 8, Aug. 2007, pp. 926-931.
Dubberke et al., "Burden of Clostridium difficile on the healthcare system", Clinical Infectious Diseases, vol. 55, suppl. 2, Aug. 2012, pp. S88-S92.
Dupont, HL., "The search for effective treatment of Clostridium difficile infection", The New England Journal of Medicine, vol. 364, No. 5, Feb. 3, 2011, pp. 473-475.
Fu et al., "Simplified purification method for Clostridium difficile toxin A", World J. Gastroenterology, vol. 10, No. 18, Sep. 15, 2004, pp. 2756-2758.
Giannasca et al., "Active and passive immunization against Clostridium difficile diarrhea and colitis", Vaccine, vol. 22, No. 7, Feb. 17, 2004, pp. 848-856.
Greenberg et al., "Phase I dose finding studies of an adjuvanted Clostridium difficile toxoid vaccine", Vaccine, vol. 30, No. 13, Mar. 16, 2012, pp. 2245-2249.
Guillemin et al., "Patients' experience and perception of hospital-treated Clostridium difficile infections: a qualitative study", The Patient-Patient-Centered Outcomes Research, vol. 7, No. 1, Mar. 2014, pp. 97-105.
Hurst et al., Organisation for Economic Co-operation and Development Working Paper: "Tackling excessive waiting times for elective surgery: a comparison of policies in twelve OECD countries", DELSA/ELSA/WD/HEA, vol. 6, ANN1, Jul. 7, 2003, Available from: http://www.oecd.org/els/health-systems/5163379.pdf.
International Search Report and Written Opinion received for International PCT application No. PCT/US2014/042298, dated Mar. 11, 2014, 12 pages.
Keel et al., "The Distribution and Density of Clostridium difficile Toxin Receptors on the Intestinal Mucosa of Neonatal Pigs", Vet. Pathol, vol. 44, No. 6, Nov. 2007, pp. 814-822.
Kelly et al., "The host immune response to Clostridium difficile", Journal of Medical Microbiology, vol. 60, pt 8, Aug. 2011, pp. 1070-1079.

(Continued)

*Primary Examiner* — Brian J Gangle
(74) *Attorney, Agent, or Firm* — Patrick J. Halloran

(57) ABSTRACT

This disclosure relates to methods for eliciting an immune response against *C. difficile* toxin A and toxin B in an adult human subject. The subject may be at risk for a primary symptomatic *C. difficile* infection. In some embodiments, a method is for eliciting an immune response against *C. difficile* toxin A and toxin B in an adult human subject at risk for a primary symptomatic *C. difficile* infection, and comprises administering to the subject a composition comprising *C. difficile* toxoid A and toxoid B at least three times, each administration being about seven days apart.

22 Claims, No Drawings

(56) References Cited

OTHER PUBLICATIONS

Kotloff et al., "Safety and immunogenicity of increasing doses of a Clostridium difficile toxoid administered to healthy adults", Infect Immun., vol. 69, No. 2, Feb. 2001, pp. 988-995.
Kuijper et al., "Emergence of Clostridium difficile-associated disease in North America and Europe", Clinical Microbiology and Infection, vol. 12, suppl. 6, Oct. 2006, pp. 2-18.
Kutty et al., "Risk factors for and estimated incidence of community-associated Clostridium difficile infection", North Carolina, USA, Emerging Infectious Diseases, vol. 16, No. 2, Feb. 2010, pp. 197-204.
Kyne et al., "Clostridium difficile", Gastroenterology Clinics of North America, vol. 30, No. 3, Sep. 2001, pp. 753-777, ix-x.
Kyne et al., "Association between antibody response to toxin A and protection against recurrent Clostridium difficile diarrhoea", Lancet., vol. 357, No. 9251, Jan. 20, 2001, pp. 189-193.
Kyne et al., "Asymptomatic carriage of Clostridium difficile and serum levels of IgG antibody against toxin A", The New England Journal of Medicine, vol. 342, No. 6, Feb. 10, 2000, pp. 390-397.
Lancaster et al., "An assessment of thermal stability of Clostridium difficile toxoid formulations", Human Vaccines, vol. 7, No. 2, Feb. 1, 2011, pp. 202-210.
Lessa et al., "Burden of Clostridium difficile infection in the United States", The New England Journal of Medicine, vol. 372, No. 9, Feb. 26, 2015, pp. 825-834.
Libby et al., "Effects of the two toxins of Clostridium difficile in antibiotic-associated cecitis in hamsters", Inf. Immun., vol. 36, No. 2, May 1982, pp. 822-829.
McFarland et al., "Breaking the cycle: treatment strategies for 163 cases of recurrent Clostridium difficile disease", The American Journal of Gastroenterology, vol. 97, No. 7, Jul. 2002, pp. 1769-1775.
Meador et al., "Purification and characterization of toxin B from Clostridium difficile", Infect. Immun., vol. 56, No. 7, Jul. 1988, pp. 1708-1714.
Newcombe, RG., "Two-sided confidence intervals for the single proportion: comparison of seven methods", Statistics in Medicine, vol. 17, No. 8, Apr. 30, 1998, pp. 857-872.
O'Brien et al., "The emerging infectious challenge of clostridium difficile-associated disease in Massachusetts hospitals: clinical and economic consequences", Infection Control and Hospital Epidemiology, vol. 28, No. 11, Nov. 2007, pp. 1219-1227.
Rothman et al., "Differential cytotoxic effects of toxins A and B isolated from Clostridium difficile", Infect. Immun., vol. 46, No. 2, Nov. 1984, pp. 324-331.
Rupnik et al., "Clostridium difficile infection: new developments in epidemiology and pathogenesis", Nature Reviews Microbiology, vol. 7, No. 7, Jul. 2009, pp. 526-536.
Sougioultzis et al., "Clostridium difficile toxoid vaccine in recurrent C. difficile-associated diarrhea", Gastroenterology, vol. 128, No. 3, Mar. 2005, pp. 764-770.
Sullivan et al., "Purification and Characterization of Toxins A and B of Clostridium difficile", Infect. Immun., vol. 35, No. 3, Mar. 1982, pp. 1032-1040.
Vaishnavi, C., "Clinical spectrum & pathogenesis of Clostridium difficile associated diseases", The Indian Journal of Medical Research, vol. 131, Apr. 2010, pp. 487-499.
Wang, et al., "A chimeric toxin vaccine protects against primary and recurrent Clostridium difficile infection", Infect Immun., vol. 80, No. 8, Aug. 2012, pp. 2678-2688.
International Search Report and Written Opinion received for International PCT application No. PCT/US2014/029035, dated Sep. 15, 2015, 15 pages.
International Search Report and Written Opinion received for International PCT application No. PCT/US2014/029070, dated Sep. 15, 2015, 13 pages.
Bartlett, et al. Clinical recognition and diagnosis of Clostridium difficile infection. Clin Infect Dis. 46 Suppl 1:S12-8.:S12-S18 (2008).
Bauer, et al. Clostridium difficile infection in Europe: a hospital-based survey. The Lancet, 377(9759): 63-73 (2010).
Cohen, et al. Clinical practice guidelines for Clostridium difficile infection in adults: 2010 update by the society for healthcare epidemiology of America (SHEA) and the infectious diseases society of America (IDSA). Infect Control Hosp Epidemiol. 31: 431-455 (2010).
Gravel, et al. Health care-associated Clostridium difficile infection in adults admitted to acute care hospitals in Canada: a Canadian Nosocomial Infection Surveillance Program Study. Clin Infect Dis. 48: 568-576 (2009).
Kelly, et al. Clostridium difficile—more difficult than ever. N Eng J Med. 359: 1932-1940 (2008).
Landau, et al. Physicians identify clostridium difficile colitis as a serious problem in need of new immune therapies. Gastrointestinal Endoscopy 45(4) (1997).
Linevsky, et al. IL-8 release and neutrophil activation by Clostridium difficile toxin-exposed monocytes. Am J Physiol. 273: G1333-G1340 (1997).
Metz, et al. Identification of Formaldehyde-induced Modifications in Proteins. J. Biol. Chem. 279(8): 6235-6243 (2004).
Murphy, et al. Frequent hospital readmissions for Clostridium difficile Infection and the Impact of Estimates of Hospital-Associated C. difficile Burden. Infect Control Hosp Epidemiology. 33:20-28 (2012).
Warny, et al. Human antibody response to Clostridium difficile toxin A in relation to clinical course of infection. Infect Immun. 62: 384-389 (1994).
Warny, et al. Pathogenesis of Clostridium difficile toxins. In: Hecht GA, editor. Microbial pathogens and the Intestinal epithelial cell. American Society for Microbiology Press, Chapter 27, p. 503-524 (2003).
Adaljia, et al. Clostridium difficile: moving beyond antimicrobial therapy. Critical Care, 14:320-21 (2010).
Lowy, et al. Treatment with Monoclonal Antibodies against Clostridium difficile Toxins. N. Eng. J. Med., 362(3): 197-205 (2010).
Foglia et al., "Clostridium difficile: development of a novel candidate vaccine", Vaccine, vol. 30, No. 29, Jun. 19, 2012, pp. 4307-4309.
Centers for Disease Control and Prevention, Food and Drug Administration, National Institutes of Health. Report of the Emerging Clostridial Disease Workshop, May 11, 2006: Summary of Proceedings. Atlanta, GA: Department of Health and Human Services (2006).
International Search Report and Written Opinion received for International PCT application No. PCT/US2014/042298, dated Mar. 11, 2014, 3 pages.
Lowy, et al. Treatment with Monoclonal Antiboies against Clostridium difficile Toxoids. New Eng. J. Med. 362(3): 197-205 (2010).

COMPOSITIONS AND METHODS FOR IMMUNIZING AGAINST C. DIFFICILE

RELATED APPLICATIONS

This application is the National Stage Application under 35 U.S.C. §371 of International Application No. PCT/US2014/042298 filed Jun. 13, 2014, which claims priority to U.S. Ser. No. 61/835,246 filed Jun. 14, 2013, the entire contents of which are incorporated into this disclosure.

FIELD OF THE DISCLOSURE

This disclosure relates to methods for eliciting an immune response against *C. difficile* toxin A and toxin B in an adult human subject (e.g., an adult human being at risk for a primary symptomatic *C. difficile* infection).

BACKGROUND OF THE DISCLOSURE

*Clostridium difficile* (*C. difficile*) is a gram-positive spore-forming, anaerobic bacteria. Pathological effects of *C. difficile* are mediated by the secreted toxins A and B, which cause colonic mucosal injury and inflammation. Although *C. difficile* infection (CDI) is asymptomatic in some patients, CDI may result in acute diarrhea and colitis, and in severe cases can lead to pseudomembranous colitis and toxic megacolon. *C. difficile* is a clinically important cause of nosocomial diarrhea and colitis in hospitalized patients receiving drugs that alter normal gut flora, and CDI is increasingly reported in the community. Risk factors for symptomatic *C. difficile* infection include antibiotic treatment, advanced age, underlying illness, and hospitalization or residence in a long-term care facility.

Early phase clinical trials have been conducted to evaluate the safety and immunogenicity of versions of *C. difficile* toxoid vaccines. In healthy adult (18-55 years old) and elderly (≥65 years old) volunteers, an earlier evaluated *C. difficile* vaccine comprising toxoid A and B proved safe and elicited an immune response to both toxin A and toxin B (Greenberg, et al. Vaccine 30: 2245-2249 (2012); Foglia, et al. Vaccine, 30: 4307-4309 (2012)). The maximal dose in such studies was 50 µg and the toxin A to toxin B ratio 3:1. The candidate vaccine was administered on days 0, 28 and 56. Seroconversion to toxin A was higher than toxin B after multiple doses in both the healthy adult and elderly volunteer groups and a more rapid decline in the antibody response in elderly subjects as compared to the younger group was observed. Those of ordinary skill in the art recognize this as a significant problem as the elderly are often immunocomprised. The need for a *C. difficile* vaccine for use in adults at risk of a symptomatic *C. difficile* infection continues, especially in the elderly.

SUMMARY OF THE DISCLOSURE

This disclosure relates to methods for eliciting an immune response against *C. difficile* toxin A and toxin B in an adult human subject (e.g., an adult at risk for a primary symptomatic *C. difficile* infection). In some embodiments, the methods may comprise administering to the subject a composition (e.g., a vaccine) comprising an effective amount of *C. difficile* toxoid A and toxoid B (e.g., about 40 to about 500 µg/dose, total amount of toxoids A and B in the composition)) at an effective toxoid A:B ratio (e.g., about any of 3:1, 3:2, or 1:1 toxoid A to toxoid B by weight), and with a sufficient purity (e.g., at least about 50 to about 100%, such as about 90-100% (w/w)), using one or more administrations (e.g., three times) by any suitable route (e.g., intramuscularly), each dose of a multiple dose administration regimen being suitably separated from one another as may be determined by one of ordinary skill in the art as described herein (e.g., by about one to 10 days apart such as about seven days). In one embodiment, the method may comprise first, second and third administrations wherein the second administration is about seven days after the first administration and the third administration is at least about 30 days and/or at least about 180 days after the first and/or second administration. In preferred embodiments of a multi-dose regimen, the first dose may be administered about seven days after the first dose, and/or a third dose is administered about 30 days after the first dose (or about 20-25 days after the second dose). In some embodiments, the method may comprise one or more adjuvants (e.g., an aluminum adjuvant). In certain embodiments, the method may comprise administering the composition to a human subject at risk for infection. In some embodiments, the human subject may be at least about any of 40, 50, 65 years or older. In some embodiments, the human subject may be about 40 to about 65 years of age. In some embodiments, the human subject may be about 65-75 years of age or older. In certain such embodiments, that human subject may have had, in the 12 month period before the first administration, at least one or two hospital stays, each lasting at least about any of 24, 48 or 72 hours or more, and had received systemic (not topical) antibiotics; and/or, is anticipated to have an in-patient hospitalization for a planned surgical procedure within 60 days of the first administration. In some embodiments, the anticipated/impending hospital stay/hospitalization may be planned to be for 72 hours or more and may be for a surgery involving at least one of the kidney/bladder/urinary system, musculoskeletal system, respiratory system, circulatory system, and/or central nervous system. It is preferred that the immune response elicited by these methods is sufficient to prevent and/or treat and/or ameliorate and/or reduce the risk of symptomatic *C. difficile* infection. One of ordinary skill in the art may derive other embodiments from the description provided herein.

DETAILED DESCRIPTION

This disclosure relates to compositions and methods that may be used to treat, ameliorate, reduce the risk of, and/or prevent symptomatic infection by *C. difficile*. As described above, those of ordinary skill in the art have encountered difficulty designing efficacious vaccines against infections caused by *C. difficile*. An efficacious vaccine may be one that, for instance, treats, ameliorates, reduces the risk of and/or prevents symptomatic infection by *C. difficile*. These problems have been surprisingly solved by the compositions and methods described herein. Various embodiments of these surprisingly effective solutions are described herein. Exemplary compositions are provided. For instance, compositions comprising an effective amount of *C. difficile* toxoid A and toxoid B (e.g., from about 40 to about 500 µg/dose, such as about any of 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 µg/dose, such as about 50 to about 100 µg/dose (w/w, total amount of toxoids A and B in the composition)) at an effective toxoid A:B ratio (e.g., about any of 10%, 20%, 30%, 40%, 50%, 60%, 70%, 3:1, 3:2, or 1:1 toxoid A to toxoid B by weight), and with a sufficient purity (e.g., at least about 50 to about 100%, such as about any of 50, 55 60, 65, 70, 75, 80, 85, 90, 95 or 90-100% (w/w)), using one or more administrations (e.g., three administrations or doses) by any suitable route (e.g., intramuscularly), each dose of a multiple dose administration regimen being suitably separated from one another (e.g., by at least about one to about ten days such as about any of one, two, three, four, five, six, seven, eight, nine or ten, such as about seven days) are provided. The length of time (time interval) between doses would be understood by those of ordinary skill to vary depending on the individual and that that interval should be long enough (e.g., as measured in days) such that the immune response from the prior dose both has time to develop (e.g., to be primed) and is not in any way inhibited by the subsequent dose (e.g., the boosting dose or doses). For example, one particular individual may require at least about seven days (e.g., 5-8 days) between doses while another may only require at least about four days (e.g., 3-5 days). In some embodiments, then, the dosing interval may vary by, for example, about 10-20%. Those of ordinary skill in the art would understand that the time between doses may need to be adjusted as described herein. In some embodiments, the second administration is at least one, two, three, four, five, six, seven, eight, nine or ten days after the first administration (e.g., day 0) and the third administration is at least about 20-200 (e.g., about 20, 30, 40, 50, 60, 70, 80, 90, 100, 110, 120, 130, 140, 150, 160, 170, 180, 190, or 200, such as about 30 or about 180 days) days after the first administration. For instance, the method may comprise first, second and/or third administrations wherein the second administration is at least 7 days after the first administration and the third administration is at least about 30 days and/or at least about 180 days after the first or second administration. In some embodiments, the second administration is about seven days after the first administration and the third administration is about 30 days after the first administration. Upon administration of such compositions using such methods to a host/subject, an immune response is typically observed, which typically includes a humoral immune response and may involve a cellular immune response. In certain embodiments, the method may comprise administering the immunogenic composition to a human, subject at risk for infection. In some embodiments, the human subject may be at least about any of 40, 50, 65 years or older. In some embodiments, the human subject may be about 40 to about 65 years of age. In some embodiments, the human subject may be 65-75 years of age. Thus, methods for administering the compositions are also provided. Methods for making the compositions are described herein and are available to those of ordinary skill in the art. Other embodiments will be clear from the descriptions provided herein.

This disclosure also describes methods for immunizing a subject (e.g., a human being) against *C. difficile* by administering thereto a composition comprising one or more antigens of *C. difficile*. For instance, a suitable composition may comprise a total of about 50 or about 100 μg (or about 50-100 μg) *C. difficile* toxoid (toxoid A and toxoid B) at an approximate toxoid A to toxoid B ratio of about 3:2, with or without adjuvant (e.g., aluminum hydroxide). For comparison purposes, the antigen-containing composition may be administered to one group of subjects and a placebo composition (e.g., 0.9% normal saline) administered (e.g., on the same schedule) to another group. Immunological data and safety data may be obtained from the subjects on particular days (e.g., days 0, 14, 30, 60, 180, and/or 210, and/or up to 1000 days after the first administration). Administration of the composition may take place on, for example, days 0 (first administration), about day 7 (second administration), about day 30 (third administration) and/or about day 180 (alternative third administration or fourth administration).

As mentioned above, the composition may comprise *C. difficile* toxoid A and toxoid B at an effective toxoid A:B ratio (e.g., about any of 3:1, 3:2, or 1:1 toxoid A to toxoid B by weight) at a sufficient purity (e.g., about 90% or higher purity (w/w)). For instance, the composition may comprise a highly purified (e.g., >90% (w/w) preparation of *C. dfficile* toxoids A & B in an approximate toxoid A to toxoid B ratio of about 3:2. Such compositions may be prepared using any of the available methods of preparation (e.g., as described in U.S. Prov. Appln. Ser. Nos. 61/790,423 filed Mar. 15, 2013, co-pending PCT/US2014/029035 filed Mar. 14, 2014, 61/793,376 filed Mar. 15, 2013, and/or co-pending PCT/US2014/029070 filed Mar. 14, 2014), each of which being hereby incorporated into this disclosure in their entirety). As described in the Examples of this disclosure, toxins A and B were purified from cultures of *C. difficile*, inactivated, and mixed at targeted 3:2 ratio and shown to be efficacious in inducing and/or enhancing the immune response against *C. difficile* toxins A and B As mentioned above, however, toxoids A and B may be combined at any effective amount and/or effective ratio (effective indicating, for example, that an efficacious vaccine is provided).

The term "*C. difficile* toxoid" is used herein to refer to a *C. difficile* toxin (Toxin A or Toxin B) that has been partially or completely inactivated. A toxin is inactivated if it has less toxicity (e.g., 100%, 99%, 98%, 80%, 70%, 60%, 50%, 40%, 30%, 20%, 10% or less toxicity or any value therebetween) than untreated toxin, as measured by for example an in vitro cytotoxicity assay or by animal toxicity. *C. difficile* toxoids can be produced by purification of toxins from *C. difficile* cultures and invativation of toxins by chemical (e.g., formaldehyde, glutaraldehyde, peroxide or oxygen treatment). Alternatively, wild type or mutant *C. difficile* toxins that lack or have reduced toxicity can be produced using recombinant methods. Methods of making toxoids by genetic methods are well know in the art. For example, mutations resulting in reduced toxicity can be made. Wild type or mutant *C. difficile* toxins lacking specific regions to reduce toxicity can also be made.

The composition, which may be a vaccine, may be provided as a lyophilized formulation that may be reconstituted at the clinical site with diluent, and mixed with either adjuvant (e.g., an aluminum adjuvant such as aluminum phosphate or aluminum hydroxide or water for injection (WFI), when specified. The diluent may be, for example, any pharmaceutically acceptable diluent (e.g., 20 mM Sodium Citrate, 5% Sucrose, and 0.016% Formaldehyde; 10 mM Citrate, 4% Sucrose, 0.008% Formaldehyde, 0.57% Sodium Chloride). The adjuvant may comprise, for instance, a suitable concentration (e.g., about any of 800-1600 μg/mL) of an adjuvant, such as an adjuvant comprising aluminum (e.g., aluminum hydroxide or aluminum phosphate) in WFI. For instance, the adjuvant (e.g., 800-1600 μg/mL aluminum hydroxide in 0.57% Sodium Chloride) may be used as the diluent to reconstitute the lyophilized formulation. WFI may be used to dilute the lyophilized vaccine for the unadjuvanted formulations. The final dosing solution may comprise, for instance, composition/vaccine, diluent and adjuvant. As described above, placebo may also be provided as a liquid formulation (e.g., 0.9% normal saline). The volume of each delivered dose of study drug (vaccine or placebo) may be about 0.5 mL. Formulations may be administered by any suitable route (e.g., subcutaneously, intravenously, intramuscularly, intraperitoneally, intradermally, intranodally, intranasally, orally).

The usefulness (e.g., immunogenicity) of any of the materials (e.g., compositions) and/or methods described herein may be assayed by any of the variety of methods known to those of skill in the art. Any one or more of the assays described herein, or any other one or more suitable assays, may be used to determine the suitability of any of the materials described herein for an intended purpose. It is to be understood that these methods are exemplary and non-limiting; other assays may also be suitable.

For instance, the compositions described herein typically induce and/or enhance the production of antibodies against *C. difficile* upon administration to a subject. Such antibodies may be detected in the subject using any of the methods available to those of ordinary skill in the art. For instance, as described in the Examples section, serum may be obtained from a subject and tested by ELISA to detect immunoglobulin type G (IgG) antibodies to *C. difficile* toxin A and/or toxin B (e.g., "primary immunogenicity data"). Antibodies present in test sera may be reacted with toxin A or B antigens adsorbed to individual wells of a microtiter plate. The amount of antibody bound to the antigen coated wells may be determined using a colorimetric substrate reaction after binding of a secondary anti-IgG (e.g., anti-human IgG) antibody-enzyme conjugate. Substrate for the enzyme is then typically added that causes colorimetric change that was directly proportional to the antibody bound to the antigen. The concentration of antibodies in serum may be derived by extrapolation from a standard curve, which was generated from multiple dilutions of a reference standard serum with defined IgG unitage (ELISA unit (EU)/mL)).

A toxin neutralization assay (TNA) may also be used to quantitate neutralizing antibodies to *C. difficile* toxin. In this assay, serial diluted serum may be incubated with a fixed amount of *C. difficile* toxin A or B. Test cells (e.g., Vero cells) may then added and serum-toxin-cell mixture incubated under appropriate conditions (e.g., 37° C. for 6 days). The ability of the sera to neutralize the cytotoxic effect of the *C. difficile* toxin may be determined by and correlated to the viability of the cells. The assay utilizes the accumulation of acid metabolites in closed culture wells as an indication of normal cell respiration. In cells exposed to toxin, metabolism and $CO_2$ production is reduced; consequently, the pH rises (e.g., to 7.4 or higher) as indicated by the phenol red pH indicator in the cell culture medium. At this pH, the medium appears red. Cell controls, or cells exposed to toxin which have been neutralized by antibody, however, metabolize and produce $CO_2$ in normal amounts; as a result, the pH is maintained (e.g., at 7.0 or below) and at this pH, the medium appears yellow. Therefore, *C. difficile* toxin neutralizing antibodies correlate with the ability of the serum to neutralize the metabolic effects of *C. difficile* toxin on cells as evidenced by their ability to maintain a certain pH (e.g., of 7.0 or lower). The color change of the media may be measured (e.g., at 562 nm to 630 nm) using a plate reader to further calculate the antitoxin neutralizing antibody titer at 50% inhibition of the *C. difficile* toxin-mediated cytotoxicity.

In certain embodiments, it is preferred that the compositions described herein exhibit immunogenic properties (e.g., inducing a detectable and/or neutralizing and/or protective immune response) following appropriate administration to a subject. The presence of neutralizing and/or protective immune response may be demonstrated as described above and/or by showing that infection by a pathogen (e.g., *C. difficile*) is affected (e.g., decreased) in individuals (e.g., human being or other animal) to whom the materials described herein have been administered as compared to individuals to whom the materials have not been administered. For instance, one or more test subjects (e.g., human or non-human) may be administered by any suitable route and schedule a composition described herein, and then after a suitable amount of time (e.g., about 1, 2, 3, 4, 5, 6, 7, 8, 9, or 10 weeks) challenged by a pathogenic organism. The animal(s) may be monitored for immune function (e.g., antibody production, T cell activity) following administration and/or challenge. Sera may be analyzed for total antibody response or for expression of particular subtypes using, for example, an antibody ELISA and/or a pathogen neutralization assay. T cell activity may be measured by, for example, measuring IFN-γ production after re-stimulation with the antigen. Statistical analysis (e.g., Fisher's exact test, Wilcoxon test, Mann-Whitney Test) may then be performed on data to determine whether the effectiveness of the material in affecting the immune response.

The *C. difficile* toxoids A and/or B as described herein may be combined with one or more pharmaceutically acceptable carriers to provide a composition prior to administration to a host. A pharmaceutically acceptable carrier is a material that is not biologically or otherwise undesirable, e.g., the material may be administered to a subject, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. Suitable pharmaceutical carriers and their formulations are described in, for example, *Remington's: The Science and Practice of Pharmacy*, 21$^{st}$ Edition, David B. Troy, ed., Lippicott Williams & Wilkins (2005), and may be appropriate Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained-release preparations such as semipermeable matrices of solid hydrophobic polymers containing polypeptides or fragments thereof. Matrices may be in the form of shaped articles, e.g., films, liposomes or microparticles. It will be apparent to those persons skilled in the art that certain carriers may be more preferable depending upon, for instance, the route of administration and concentration of composition being administered. Carriers are those suitable for administration to humans or other subjects.

Pharmaceutical compositions may also include thickeners, diluents, buffers, preservatives, surface active agents, adjuvants, immunostimulants. Pharmaceutical compositions may also include one or more active ingredients such as antimicrobial agents, antiinflammatory agents and anesthetics. Adjuvants (e.g., as described herein or as may be otherwise available) may also be included to stimulate or enhance the immune response.

As described above, the compositions may also comprise one or more adjuvants. Adjuvants may be included to stimulate or enhance the immune response. Non-limiting examples of suitable classes of adjuvants include those of the gel-type (i.e., aluminum hydroxide/phosphate ("alum adjuvants"), calcium phosphate, microbial origin (muramyl dipeptide (MDP)), bacterial exotoxins (cholera toxin (CT), native cholera toxin subunit B (CTB), *E. coli* labile toxin (LT), pertussis toxin (PT), CpG oligonucleotides, BCG sequences, tetanus toxoid, monophosphoryl lipid A (MPLA) of for example, *E. coli, Salmonella minnesota, Salmonella typhimurium,* or *Shigella exseri*), particulate adjuvants (biodegradable, polymer microspheres), immunostimulatory complexes (ISCOMs)), oil-emulsion and surfactant-based adjuvants (Freund's incomplete adjuvant (FIA), microfluidized emulsions (MF59, SAF), saponins (QS-21)), synthetic (muramyl peptide derivatives (murabutide, threony-MDP), nonionic block copolymers (L121), polyphosphazene (PCCP), synthetic polynucleotides (poly A:U, poly I:C), thalidomide derivatives (CC-4407/ACTIMID)), RH3-ligand, or polylactide glycolide (PLGA) microspheres, among others. Fragments, homologs, derivatives, and fusions to any of these toxins are also suitable, provided that they retain adjuvant activity. Suitable mutants or variants of adjuvants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that may used include, for example, Ser-63-Lys, Ala-69-Gly,Glu-110-Asp, and Glu-112-Asp mutants. Metallic salt adjuvants such as alum adjuvants are well-known in the art as providing a safe excipient with adjuvant activity. The mechanism of action of these adjuvants are thought to include the formation of an antigen depot such that antigen may stay at the site of injection for up to 3 weeks after administration, and also the formation of antigen/metallic salt complexes which are more easily taken up by antigen presenting cells. In addition to aluminium, other metallic salts have been used to adsorb antigens, including salts of zinc, calcium, cerium, chromium, iron, and berilium. The hydroxide and phosphate salts of aluminium are the most common. Formulations or compositions containing aluminium salts, antigen, and an additional immunostimulant are known in the art. An example of an immunostimulant is 3-de-O-acylated monophosphoryl lipid A (3D-MPL). In some embodiments, the one or more adjuvants may be any one or more of an aluminum salt, emulsion, liposome, polymer, and/or a combination thereof. For instance, suitable adjuvants may include any one or more of anionic polymers, adjuvants comprising liposomes and Toll-like 7/8 receptor agonists, ethyl DOPC liposomes, DC-chol, squalene emulsions comprising Toll-like 7/8 receptor agonists or Toll-like 4 receptor agonists, aluminum salts comprising Toll-like 4 receptor agonists. Certain of these compositions may be included in an immunogenic composition and/or vaccine (e.g., a therapeutic or preventative immunogenic composition). Other adjuvants may also be suitable as would be understood by those of skill in the art. Any of such adjuvants may be introduced into the composition either before, during or after the production process.

As referred to above, an immunological composition is typically one that comprises *C. difficile* antigen(s) and, upon administration to a host (e.g., an animal), induces or enhances an immune response directed against the antigen (and, e.g., *C. difficile*). Such responses may include the generation of antibodies (e.g., through the stimulation of B cells) or a T cell-based response (e.g., a cytolytic response), as described above, which may be protective and/or neutralizing. A protective or neutralizing immune response may be one that is detrimental to the infectious organism corresponding to the antigen (e.g., from which the antigen was derived) and beneficial to the host (e.g., by reducing or preventing infection). As used herein, protective or neutralizing antibodies and/or cellular responses may be reactive with the *C. difficile* antigen(s) described here, especially when administered in an effective amount and/or schedule. Those antibodies and/or cellular responses may reduce or inhibit the severity, time, and/or lethality of *C. difficile* infection when tested in animals. As shown in the examples, the compositions described herein may be used to induce an immune response against *C. difficile*. An immunological composition that, upon administration to a host, results in a therapeutic (e.g., typically administered during an active infection) and/or protective (e.g., typically administered before or after an active infection) and/or neutralizing immune response, may be considered a vaccine.

In some embodiments, methods for preventing, ameliorating, reducing the risk of and/or treating (e.g., affecting) infection by *C. difficile* are also provided. Methods for treating one or more disease conditions caused by or involving *C. difficile* in a subject comprising administering to the subject at least one or more effective doses of a composition described herein (e.g., comprising *C. difficile* antigens, e.g., toxoid A, toxoid B). The antigens may be administered in a dosage amount of about 1 to about 300 µg (e.g., about any of 1, 2, 3, 4, 5, 6, 7, 8, 9, 10, 15, 20, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 and/or 300 µg). The antigens may be administered more than once in the same or different dosage amounts. In certain embodiments, the *C. difficile* antigens may be administered to the subject by the same or different suitable route(s) one, two, three, four, five, six, seven, eight, nine, ten, or more times. When multiple doses are administered, the doses may comprise about the same or different type and/or amount of *C. difficile* antigens in each dose. The doses may also be separated in time from one another by the same or different intervals. For instance, the doses may be separated by about any of 6, 12, 24, 36, 48, 60, 72, 84, or 96 hours, seven days, 14 days, 21 days, 30 days, 40 days, 50 days, 60 days, 70 days, 80 days, 90 days, 100 days, 110 days, 120 days, 130 days, 140 days, 150 days, 160 days, 170 days, 180 days, 190 days, 200 days, one week, two weeks, three weeks, one month, two months, three months, four months, five months, six months, seven months, eight months, nine months, 10 months, 11 months, 12 months, 1.5 years, 2 years, 3 years, 4 years, 5 years, or any time period before, after, and/or between any of these time periods. In some embodiments, the *C. difficile* antigens may be administered alone or in conjunction with other agents (e.g., antibiotics) Such other agents may be administered simultaneously (or about simultaneously) with the same or different *C. difficile* antigens, or at a different time and/or frequency. Other embodiments of such methods may also be appropriate as could be readily determined by one of ordinary skill in the art.

Also provided herein are kits for administering the *C. difficile* antigens. In one embodiment, one or more of *C. difficile* antigens may form part of and/or be provided as a kit for administration to a subject. Instructions for administering the *C. difficile* antigens may also be provided by the kit. Compositions comprising *C. difficile* antigens as described herein may be included in a kit (e.g., a vaccine kit). For example, the kit may comprise a first container containing a composition described herein in dried form and a second container containing an aqueous solution for reconstituting the composition. The kit may optionally include the device for administration of the reconstituted liquid form of the composition (e.g., hypodermic syringe, microneedle array) and/or instructions for use. The device for administration may be supplied pre-filled with an aqueous solution for reconstituting the composition.

Thus, this disclosure provides compositions for providing a therapeutic or protective immune response against *C. difficile*, the composition comprising *C. difficile* toxoid A and toxoid B. The disclosure also provides methods for administering such compositions such that an immune response against *C. difficile* (e.g., *C. difficile* antigens) is induced and/or enhanced. In certain embodiments, the compositions may further comprise one or more *C. difficile* antigens, one or more pharmaceutically acceptable carriers and/or one or more adjuvants (e.g., aluminum salt, emulsion, cationic liposome, anionic polymer, Toll-like receptor agonist, and a combination thereof). In some embodiments, the compositions are immunogenic compositions and/or vaccines. Also provided are methods for immunizing a subject (such as a human being) by administering thereto any such compositions. In some embodiments, the methods may comprise administering to the subject an immunogenic composition (e.g., a vaccine) comprising an effective amount (e.g., at least about 40 to about 500, such about 50 to about 100 µg) of *C. difficile* toxoid A and toxoid B (combined w/w) at an effective toxoid A:B ratio (e.g., 3:1, 3:2, 1:1 by weight (w/w)), and with a sufficient purity (e.g., at least 90% (w/w)), using one or more administrations (e.g., at least three times, each dose being suitably separated from one another (e.g., at least about 7 days)). An effective toxoid A:B ratio is any ratio that may be included in a composition and induce an effective immune response against *C. difficile* toxin A and/or toxin B. In one embodiment, the method may comprise first, second and third administrations wherein the second administration is at least 7 days after the first administration and the third administration is at least about 30 days and/or at least about 180 days after the first and/or second administration. In some embodiments, the method may comprise first, second and third administrations wherein the second administration is about seven days after the first administration (on day 0) and the third administration is about 30 days after the first administration. In some embodiments, the method may comprise first, second and third administrations wherein the second administration is about seven days after the first administration and the third administration is about 180 days after the first administration. In some embodiments, the method may comprise one or more adjuvants (e.g., an aluminum adjuvant). In some embodiments, the methods may enhance and/or induce an existing immune response in a human being previously exposed to *C. difficile* (e.g., a seropositive human being, an anemnestic immune response). In certain embodiments, human being(s) may have had, in the 12 month period before the first administration, at least one or two hospital stays, each lasting at least about 24, 48 or 72 hours or more, and/or had received systemic (not topical) antibiotics; and/or, is anticipated to have an in-patient hospitalization for a planned surgical procedure within about 60 days of the first administration. In some embodiments, the anticipated/impending hospital stay/hospitalization may be planned to be for about 24, 48 to 72 hours or more and may be for a surgery involving at least one of the kidney/bladder/urinary system, musculoskeletal system, respiratory system, circulatory system, and central nervous system. It is preferred that the immune response elicited by these methods is sufficient to prevent and/or ameliorate and/or reduce the risk of symptomatic *C. difficile* infection. In certain embodiments, the method may comprise administering the immunogenic composition to a human subject at risk for a symptomatic infection that is at least about 40, 50 or 65 years of age. In some embodiments, the method may comprise administering the composition to each individual of a group aged between about 40 and about 65 years old and/or between about 65 and about 75 years old. In some embodiments, the method may induce about a two- to four-fold enhancement of an antibody-based immune response against *C. difficile* toxin A and/or toxin B in about any of 80, 85, 90, 95 or 100% of a population of individuals considered seropositive before the first administration as measured by, e.g., ELISA and/or TNA. In some embodiments, the method may induce about a two- to four-fold enhancement of an antibody-based immune response against *C. difficile* toxin A and/or toxin B in about any of 20, 25, 30, 35, 40, 45, or 50% of a population of individuals considered seronegative before administration of the composition, as measured by, e.g., ELISA and/or TNA 14 days after the first administration (e.g., following administration at days 0, seven and 30). In some embodiments, the method may induce about a two- to four-fold enhancement of an antibody-based immune response against *C. difficile* toxin A and/or toxin B in about any of 30, 35, 40, 45, 50, 55, 60, 65, 70, 75, or 80% of a population of individuals considered seronegative before administration of the composition, as measured by, e.g., ELISA and/or TNA 60 days after the first administration (e.g., following administration at days 0, seven and 30). In some embodiments, the individuals in such populations are from about 40 to about 65 years old. In some embodiments, the individuals in such populations are from about 75 to about 65 years old. In some embodiments, this enhancement is observed about 30 days after the first administration (at day 0), typically follows a second administration at about day 7, and is typically observed before the third administration (at, e.g., about day 30 or day 180). In some embodiments, the immune response may be detectable against toxin A and/or toxin B for up to about 30 months (e.g., about 1000 days) after the first, second and/or third administration in a multiple regimen administration protocol. In some embodiments, administration of a composition described herein to a human subject at day 0 (first administration), about day 7 (second administration) and about day 30 (third administration) enhances or induces an immune response against *C. difficile* toxin A and/or toxin B for up to about 30 months, or about 1000 days as measured by, e.g., ELISA and/or TNA. In some embodiments, the level of the immune response may be about at least as high on about day 1000 following the first administration as on about day 14 following the first administration of a three dose administration regimen, as measured by, e.g., ELISA and/or TNA. In some embodiments, the level of the immune response may be about at least as high on about any of days 100, 200, 300, 400, 500, 600, 700, 800, 900 and 1000 following the first administration as on about day 14 following the first administration as measured by, e.g., ELISA and/or TNA. In some embodiments, the immune response may be about two- to eight-fold above baseline (e.g., anti-toxin A and/or toxin B antibody levels at day 0, before the first administration, as measured by e.g., ELISA and/or TNA. In some embodiments, the immune response may be from about 2.5 to about 6.8-fold above baseline as measured by e.g., ELISA and/or TNA. In some embodiments, the immune response in seropositive individuals (e.g., non-naïve) is increased from baseline by a factor of about three at about day 7; about 10 to about 70 at about day 14; about 30 to about 200 at about day 30; and about 100 to about 200 at about day 60, as measured by ELISA for toxins A and/or B (e.g., following administration at days 0, 7 and 30). In some embodiments, the immune response in seropositive individuals (e.g., non-naïve) is increased from baseline by a factor of about three at about day 7; about 10 to about 100 at about day 14; about 15 to about 130 at about day 30; and about 100 to about 130 at about day 60, as measured by TNA for toxins A and/or B (e.g., following administration at days 0, seven and 30). In some embodiments, the immune response in seronegative individuals (e.g., naïve) is increased from baseline by a factor of about two at about day 14; about five to about 10 at about day 30; and about 25 to about 60 at about day 60, as measured by ELISA for toxins A and/or B (e.g., following administration at days 0, seven and 30). In some embodiments, the immune response in seronegative individuals (e.g., naïve) is increased from baseline by a factor of about two to about three at about day 14; about two to about five at about day 30; and about five to about 40 at about day 60, as measured by TNA for toxins A and/or B (e.g., following administration at days 0, 7 and 30). In some embodiments, the immune responses described herein are detected in individuals considered either seropositive or seronegative at day 0 (e.g., before the first administration). In some embodiments, such immune response are detected for both *C. difficile* toxin A and toxin Bas measured by, e.g., ELISA and/or TNA. Methods (e.g., in vitro or in vivo) for producing such *C. difficile* antigens (e.g., toxoids A and/or B), and compositions comprising the same, are also provided. Such methods may include, for example, any of those available and/or known to those of ordinary skill in the art, and/or the methods described in previously mentioned copending U.S. Prov. Appln. Ser. No. 61/790,423 filed Mar. 15, 2013, co-pending PCT/US2014/029035 filed Mar. 14, 2014, 61/793,376 filed Mar. 15, 2013, and/or co-pending PCT/US2014/029070 filed Mar. 14, 2014). One of ordinary skill in the art may derive other embodiments from the description provided herein.

Other embodiments are also provided as would be understood by those of ordinary skill in the art.

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto.

As used herein, a subject or a host is meant to be an individual. The subject can include domesticated animals, such as cats and dogs, livestock (e.g., cattle, horses, pigs, sheep, and goats), laboratory animals (e.g., mice, rabbits, rats, guinea pigs) and birds. In one aspect, the subject is a mammal such as a primate or a human.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

When the terms prevent, preventing, and prevention are used herein in connection with a given treatment for a given condition (e.g., preventing infection), it is meant to convey that the treated subject either does not develop a clinically observable level of the condition at all, or develops it less frequently than he/she would have absent the treatment. These terms are not limited solely to a situation in which the subject experiences no aspect of the condition whatsoever. For example, a treatment will be said to have prevented the condition if it is given during exposure of a subject to a stimulus that would have been expected to produce a given manifestation of the condition, and results in the subject's experiencing fewer and/or milder symptoms of the condition than otherwise expected. A treatment can "prevent" infection by resulting in the subject's displaying only mild overt symptoms of the infection; it does, not imply that there must have been no penetration of any cell by the infecting microorganism. Similarly, reduce, reducing, and reduction as used herein may be stated in connection with the risk of symptomatic infection with a given treatment (e.g., reducing the risk of a symptomatic *C. difficile* infection). For example, reduce, reducing, and reduction may typically refer to a subject that develops an infection more slowly or to a lesser degree as compared to a control or basal level of developing an infection in the absence of a treatment (e.g., administration or vaccination using antigens or compositions disclosed). A reduction in the risk of symptomatic infection may result in the subject's displaying only mild overt symptoms of the infection or delayed symptoms of infection; it does not imply that there must have been no penetration of any cell by the infecting microorganism.

All references cited within this disclosure are hereby incorporated by reference in their entirety. Certain embodiments are further described in the following examples. These embodiments are provided as examples only and are not intended to limit the scope of the claims in any way.

EXAMPLES

Example 1

A. Trial Design

A Phase II, randomized, placebo-controlled, modified double-blind (double-blind from dosage and formulation; open-label for vaccination schedule), dose-ranging, multi-center trial in adults, was conducted. Adult subjects aged 40 to 75 years who were at risk for developing *C. difficile* infection during the trial because of (i) impending hospitalization within 60 days of enrollment, or (2) current or impending residence in a long-term care facility or rehabilitation facility within 60 days of enrollment, were enrolled. Subjects with a current or prior CDI episode were excluded. Subjects were stratified by age: 40 to 65 years (50% of subjects) and 65 to 75 years (50% of subjects). The trial had two stages. Stage I tested 4 different formulations of vaccine candidate and Stage II explored different vaccination schedules using one of these formulations. In Stage I, a total of 455 subjects were enrolled and were randomized to receive one of the following formulations or placebo on Days 0, 7, and 30:

Group 1: Low dose (a total of 50 μg antigen (Toxoid A, Toxoid B), with an approximate ratio of 3:2 for Toxoid A to Toxoid B) with adjuvant (400 μg aluminium hydroxide (ALOH));

Group 2: Low dose (a total of 50 μg antigen (Toxoid A, Toxoid B), with an approximate ratio of 3:2 for Toxoid A to Toxoid B), no adjuvant;

Group 3: High dose (a total of 100 μg antigen (Toxoid A, Toxoid B), with an approximate ratio of 3:2 for Toxoid A to Toxoid B) with adjuvant (400 μg ALOH);

Group 4: High dose (a total of 100 μg antigen (Toxoid A, Toxoid B), with an approximate ratio of 3:2 for Toxoid A to Toxoid B), no adjuvant; and, Group 5: placebo (0.9% normal saline).

Based on immunological results of blood samples and safety data taken on Days 0, 14, 30 and 60, one formulation was selected for use in Stage II. In Stage II, 206 subjects were randomized to receive 3 doses of the selected formulation on one of two additional schedules:

Group 6: Days 0, 7, and 180

Group 7: Days 0, 30 and 180.

Results from subjects enrolled in Stage II were compared with data obtained for subjects who received the selected vaccine formulation on Days 0, 7 and 30 during Stage I of the study. In Stage I, subjects were asked to provide blood samples on Days 0, 7, 14, 30, up to Day 60 and including Days 180 and 210 until a formulation was selected. In Stage II, all subjects were asked to provide blood samples on Days 0, 7, 14, 30, 60, 180, and 210.

The evaluated vaccine was a highly purified preparation of *C. difficile* Toxoids A & B (in an approximate ratio of 3:2 for Toxoid A to Toxoid B). Toxins A and B were purified from cultures of *C. difficile*, inactivated, and mixed at targeted 3:2 ratio. The vaccine was provided as a lyophilized formulation that was reconstituted at the clinical site with diluent, and mixed with either ALOH adjuvant or water for injection (WFI), when specified. The diluent consisted of 20 mM sodium citrate, 5% sucrose, and 0.016% formaldehyde. The adjuvant consisted of 1600 μg/mL ALOH in WFI. WFI was used to dilute the lyophilized vaccine for the unadjuvanted formulations. The final vaccine dosing solution consisted of vaccine and diluent and adjuvant (when necessary). Placebo was provided as a liquid formulation (0.9% normal saline). The volume of each delivered dose of study drug (vaccine or placebo) was 0.5 mL. Vaccine formulations were administered intramuscularly.

Serum was tested by ELISA for immunoglobulin type G (IgG) antibodies to *C. difficile* toxin A and toxin B to generate primary immunogenicity data. Antibodies present in test sera were reacted with toxin A or B antigens adsorbed to individual wells of a microtiter plate. The amount of antibody bound to the antigen coated wells was determined by a colorimetric substrate reaction after the binding of a secondary anti-human IgG antibody-enzyme conjugate. Substrate for the enzyme was added which caused colorimetric change that was directly proportional to the antibody bound to the antigen. The concentration of antibodies in serum was derived by extrapolation from a standard curve, which was generated from multiple dilutions of a reference standard serum with defined IgG unitage (ELISA unit (EU)/mL).

A toxin neutralization assay was also used to quantitate neutralizing antibodies to *C. difficile* toxin. In assay, serial diluted serum was incubated with a fixed amount of *C. difficile* toxin A or B. Vero cells were then added and serum-toxin-cell mixture was incubated at 37° C. for 6 days. The ability of the sera to neutralize the cytotoxic effect of the *C. difficile* toxin was determined by and correlated to the viability of the Vero cells. The assay utilized the accumulation of acid metabolites in closed culture wells as an indication of normal cell respiration. In cells exposed to toxin, metabolism and $CO_2$ production was reduced; consequently, the pH rose to 7.4 or higher as indicated by the phenol red pH indicator in the cell culture medium. At this pH, the medium appeared red. Cell controls, or cells exposed to toxin which had been neutralized by antibody, however, metabolized and produced $CO_2$ in normal amounts; as a result, the pH was maintained at 7.0 or below. At this pH, the medium appeared yellow. Therefore, *C. difficile* toxin neutralizing antibodies correlated with the ability of the serum to neutralize the metabolic effects of *C. difficile* toxin on cells as evidenced by their ability to maintain a pH of 7.0 or lower. The color change of the media could be measured at 562 nm to 630 nm by a plate reader to further calculate the antitoxin neutralizing antibody titer at 50% inhibition of the *C. difficile* toxin-mediated cytotoxicity. The study included an observational objective namely, to describe the first-time occurrence of CDI episodes.

B. Stage I

Safety Assessment

There were no related SAEs or deaths reported for subjects in any treatment group and the number of solicited or unsolicited Grade 3 reactions was similar and minimal among all treatment groups. The solicited adverse reactions (ARs) and unsolicited AEs were generally Grade 1 in intensity, of short duration, did not lead to study discontinuations and were not considered clinically significant. There were more solicited injection site and systemic reactions in the vaccine treatment groups; however, the tolerability profile was acceptable and similar or better than the tolerability profile of other licensed vaccines. Unsolicited non-serious ARs in the SOC of general disorders and administration site conditions, specifically for unsolicited injection site reactions, were reported by more subjects in the adjuvanted groups than the unadjuvanted groups; however, the tolerability profile was acceptable and similar or better than the tolerability profie of other licensed vaccines. Overall, subjects in the older age group (aged 65-75 years) did not experience increased solicited ARs or unsolicited AEs; the safety summary was similar to that of younger subjects aged 40-64 years. As with the younger subjects, there were slightly more subjects who reported AEs and ARs in the adjuvanted groups; however, the tolerability profile was acceptable. No safety concerns were identified.

Immunogenicity Assessment

There was a treatment effect noted among all vaccine groups compared to placebo.

ELISA Results—Geometric Mean Concentrations (GMCs)

Immune responses in all treatment groups were robust and continued to increase at Day 60. For both toxin A and toxin B, the highest GMCs (EU/mL) in each active vaccine group were seen on Day 60, 30 days after the third vaccine dose. There was a consistent rise in GMCs at each blood sampling day from Day 0 through Day 60 (Table 1). GMCs for toxin A and toxin B increased from Day 0 to Day 60 for subjects aged 40 to 64 years and subjects aged 65 to 75 years. GMCs tended to be higher for subjects aged 65 to 75 years when vaccine with adjuvant was administered. The number of subjects who were seropositive (defined as ≥1.5 EU/mL for toxin A and ≥0.8 EU/mL for toxin B) at baseline was higher for toxin B than for toxin A which may represent prior exposure and/or assay sensitivity. Seropositivity at baseline enhanced the immune response for toxins A and B at Day 60.

ELISA Results—Seroconversion Group 3 subjects had the highest percentage (97.3% for toxin A and 91.8% for toxin B) of all subjects in the per-protocol population who demonstrated a 4-fold seroconversion at Day 60 compared to Day 0. For the composite of toxin A and B (defined as a subject who seroconverted for both toxins A and B), the number and percentage of all subjects in Group 3 who seroconverted with a ≥4-fold rise in IgG between Day 0 and Day 60 was 90.4% (66/73). This was higher than Group 1 (85.7%; 60/70), Group 2 (82.4%; 56/68), and Group 4 (86.1%; 62/72). For the composite of toxin A and B, the number and percentage of subjects aged 65 to 75 years in Group 3 who seroconverted with a ≥4-fold rise in IgG between Day 0 and Day 60 was 89.1% (41/46). This was higher than Group 1 (77.3%; 34/44), Group 2 (71.1%; 32/45), and Group 4 (73.8%; 31/42). In the Full Analysis Set For Immunogenicity (FASI), for toxin A, the number and percentage of subjects in each group who seroconverted with a ≥4-fold rise in IgG between Day 0 and Day 60 was as follows: Group 1 94.3% (82/87); Group 2 88.3% (83/94); Group 4 88.6% (78/88); Group 5 6.3% (3/48). For toxin B, the number and percentage of subjects in each group who seroconverted with a ≥4-fold rise in IgG between Day 0 and Day 60 was as follows: Group 1 87.5% (77/88); Group 2 77.7% (73/94); Group 4 91.1% (82/90); Group 5 12.5% (6/48). For the composite of toxin A and B, the number and percentage of subjects in each group who seroconverted with a ≥4-fold rise in IgG between Day 0 and Days 60, 180 and 210 is set out in Table 2.

Toxin Neutralization Assay (TNA) Results—GMTs

For both toxin A and toxin B, the highest GMTs in each active vaccine group were seen on Day 60, 30 days after the third vaccine dose. There was a consistent rise in GMTs at each blood sampling day from Day 0 through Day 60. For toxin A, GMTs were higher in Group 1 and Group 3. The highest GMTs were seen on Day 60 in Group 3. For toxin B, GMTs were similar in Group 1 and Group 2. GMTs were higher when high dose vaccine was administered than when low dose was administered. The highest GMTs were seen on Day 60 in Group 4.

TNA Results—Seroconversion

For toxin A, Group 3 subjects had the highest percentage (97.3%) of subjects who demonstrated a 4-fold seroconversion at Day 60 compared to Day 0. Group 4 subjects had the highest percentage of subjects who demonstrated a 4-fold seroconversion at Day 60 compared to Day 0 for toxin B (66.2%) and for the composite of toxin A and B (63.5%). For the composite of toxin A and B, the number and percentage of subjects in each group in the FASI who seroconverted with a ≥4-fold rise in IgG between Day 0 and Days 60, 180 and 210 is set out in Table 2.

Stage I Conclusion

No safety concerns were identified and thus, no treatment group was eliminated from further evaluation based on safety reasons. Results from Stage I supported the safety of the vaccine in all treatment groups.

Overall, the higher doses induced the best immune response as measured by both ELISA and toxin neutralization assay (TNA). High-dose plus adjuvant vaccine induced the best immune response as measured by ELISA, particularly in the group aged 65 to 75 years. The high-dose plus adjuvant (Group 3) was selected for progression to Stage II as the tolerability profile was acceptable and the overall immune responses were considered preferable, particularly in the group aged 65-75 years. As older individuals are likely to be a major portion of the target population for the administration of a vaccine against symptomatic C. difficile infection (CDI), choosing this dose is likely to provide the maximum vaccine protection.

Based on safety and immunogenicity results (including bootstrap analyses) through Day 60 as determined during Stage I, the formulation 100 µg+ALOH (Group 3) was selected as the preferred formulation to be carried forward into Stage II. This selection was influenced by the composite ELISA ranking analysis for all subjects in the per-protocol analysis set for immunogenicity (PPSI). Particularly for subjects aged 65 to 75 years in the full analysis set for immunogenicity (FASI), Group 3 (high dose vaccine plus adjuvant) was determined to be the best formulation. Importantly, more subjects (number and percentage) in the high dose plus adjuvant group demonstrated a 4-fold seroconversion between Day 0 and Day 60 than the other groups.

Data for Group 3 from Day 0 through Day 210, together with data for Groups 6 and 7 are presented below under heading, "Stage 2". Following selection of the Stage II formulation, safety data continued to be collected between Day 60 and Day 210 for Groups 1 through 5. Two additional blood samples were obtained for immunogenicity testing on Days 180 and 210. For Groups 1, 2, and 4, the GMCs (measured by ELISA) and GMTs (measured by TNA) for both toxin A and toxin B increased from Day 0 through Day 60, reached a peak on Day 60, then decreased through Day 210. However, the Day 210 values remained high compared to baseline. At Day 210 GMCs for toxin A were approximately equal to the GMCs on Day 30 and GMCs for toxin B were approximately equal to GMCs on Day 14. At Day 210 the GMTs for toxin A and toxin B were approximately half the GMTs on Day 60. GMT Day 0 baseline values were measured for each group. There were virtually no changes from baseline for GMCs or GMTs measured in Groups 5 (placebo).

The highest ≥4-fold rise in seroconversion for the ELISA composite of toxin A and B was seen on Day 60 versus Day 0 in each of Groups 1, 2, and 4. Although the seroconversion decreased after Day 60, it remained high at Day 210, with 68.9% (51/74) of subjects in Group 1, 47.4% (36/76) of subjects in Group 2, and 64.9% (48/74) of subjects in Group 4. The highest ≥4-fold rise in seroconversion for the TNA composite of toxin A and B was seen on Day 60 versus Day 0 in each of Groups 1, 2, and 4. Although the seroconversion decreased after Day 60, it remained high at Day 210, with 39.7% (29/73) of subjects in Group 1, 40.8% (31/76) of subjects in Group 2, and 58.1% (43/74) of subjects in Group 4. On the basis of all Stage I data through Day 210, the overall conclusions reached after the Day 60 was that the selected formulation was safe and immunogenic. The low dose (i.e., 50 µg/dose, toxoids A and B in a 3:2 ratio, A:B), with or without adjuvant, provided a good immune response, particularly amongst the younger age group (i.e., 40-64 years of age).

C. Stage II

During Stage II of the study, the high dose plus adjuvant formulation (100 µg+ALOH) was evaluated using 2 additional schedules (Days 0, 7, 180; and Days 0, 30, 180). Data (through Day 210) was compared to that obtained in Group 3—that is, data was compared to that obtained in Stage I in the subject group administered the same formulation using the schedule from Stage I (Days 0, 7, 30).

1. Safety Assessment—Overview

Overall, the vaccine formulation (100 µg+ALOH) administered at 3 different schedules had an acceptable safety profile with no safety signals identified. There were no related SAEs reported for subjects in any treatment group. The number of subjects who reported solicited or unsolicited Grade 3 reactions was similar and minimal among the treatment groups. The solicited ARs and unsolicited AEs were generally Grade 1 in intensity, of short duration, did not lead to study discontinuations, and were not considered clinically significant. Solicited reactions after any vaccine injections were reported by similar numbers and percentage of subjects in the 3 groups. Unsolicited non-serious ARs (which included both injection site and systemic ARs) were reported by similar numbers and percentages of subjects in each group. Subjects in the older age group (aged 65-75 years) did not experience increased solicited ARs or unsolicited AEs; the safety summary was similar to that of younger subjects aged 40-64 years. Overall, no safety concerns were identified.

Immunogenicity Assessment

ELISA Results

For both toxin A and toxin B, the highest GMCs (EU/mL) in Groups 3 and 7 increased from Day 0 through Day 60, while in Group 6, the highest GMC was measured on Day 30. In Group 3, the GMCs decreased at Day 210, while in Groups 6 and 7, GMCs increased at Day 210, following a third vaccination at Day 180. This same pattern was seen in subjects aged 40 to 64 years and subjects aged 65 to 75 years. The number of subjects who were seropositive (defined as ≥1.5 EU/mL for toxin A and ≥0.8 EU/mL for toxin B) at baseline was higher for toxin B than for toxin A. Seropositivity at baseline enhanced the immune response for toxins A and B at Day 60 in Groups 3 and 7 or Day 30 in Group 6.

For Groups 3 and 7 for subjects in the PPSI included in the Day 210 analysis, GMCs for toxin A (measured by ELISA) increased from Day 0 through Day 60, at which point they were 96.44 EU/mL and 80.37 EU/mL, respectively. For Group 6, the highest GMC before Day 210 was reached at Day 30 (rather than Day 60), at which point it was 23.33 EU/mL. In Group 3, the GMCs decreased to 20.74 EU/mL at Day 210, while in Groups 6 and 7, GMCs increased to 266.2 EU/mL and 252.1 EU/mL, respectively, at Day 210, following a third vaccination at Day 180. For Groups 3 and 7, for subjects in the PPSI included in the Day 210 analysis, GMCs for toxin B (measured by ELISA) increased from Day 0 through Day 60, at which point they were 142.1 EU/mL and 87.65 EU/mL, respectively. For Group 6, the highest GMC before Day 210 was reached at Day 30 (rather than Day 60), at which point it was 93.59 EU/mL. In Group 3, the GMCs decreased to 26.57 EU/mL at Day 210, while in Groups 6 and 7, GMCs increased to 119.6 EU/mL and 124.7 EU/mL, respectively, at Day 210, following a third vaccination at Day 180.

There were no remarkable differences in the ELISA GMCs by subjects aged 40 to 64 years and 65 to 75 years in the FASI in Groups 3, 6, and 7 included in the Day 210 analysis.

For subjects who were seropositive at baseline, while baseline GMCs at Day 0 for both toxin A (3.75 EU/mL, 3.55 EU/mL, and 2.99 EU/mL) and B (8.65 EU/mL, 5.65 EU/mL, and 4.68 EU/mL), respectively, were low for subjects in Groups 3, 6, and 7, the GMCs tended to reach higher peak values at Days 30 or 60 than the GMCs for subjects who were seronegative at baseline.

At Day 60 for subjects in the PPSI included in the Day 210 analysis, the bootstrapping analysis identified Group 3 with at least 80% probability of being ranked number 1 for toxin B (91.5%) and the composite of toxin A and B (84.7%). At Day 60, for toxin A, an 80% probability was not reached, although Group 3 with 72.1% ranked higher than Group 6 or 7.

For toxin A (measured by ELISA) for subjects in the PPSI included in the Day 210 analysis, in Group 3, GMFR was highest (57.0) on Day 60 compared to Day 0. In Group 6, GMFR was 14.4 on Day 30 compared to Day 0, 11.3 on Day 60 compared to Day 0, but then reached 158.8 on Day 210 compared to Day 0. In Group 7, GMFR was 48.8 on Day 60 compared to Day 0, but then reached 151.4 on Day 210 compared to Day 0. For toxin B (measured by ELISA), for subjects in the PPSI included in the Day 210 analysis, in Group 3, GMFR was highest (64.2) on Day 60 compared to Day 0. In Group 6, GMFR was 43.0 on Day 30 compared to Day 0, 34.5 on Day 60 compared to Day 0, and reached 52.5 on Day 210 compared to Day 0. In Group 7, GMFR was 23.0 on Day 30 compared to Day 0, 40.1 on Day 60 compared to Day 0, and reached 53.6 on Day 210 compared to Day 0.

ELISA Results—Seroconversion

At Day 60, for toxin A, there was a ≥4-fold rise in seroconversion, measured by ELISA, for 97.0% (64/66) of subjects in Group 3, 65.6% (40/61) of subjects in Group 6, and 91.2% (52/57) of subjects in Group 7. (Subjects in Group 3 and Group 7 received a vaccination at Day 30; the last vaccination for Group 6 was at Day 7.) By contrast, at Day 60, for toxin B, the ≥4-fold rise in seroconversion, measured by ELISA, was similar across treatment groups: 92.4% (61/66) of subjects in Group 3, 85.2% (52/61) of subjects in Group 6, and 89.5% (51/57) of subjects in Group 7. At Day 60, for the composite of toxin A and B, there was a ≥4-fold rise in seroconversion, measured by ELISA, for 90.9% (60/66) of subjects in Group 3, 60.7% (37/61) of subjects in Group 6, and 84.2% (48/57) of subjects in Group 7. A summary of the ≥4-fold seroconversion rates (measured by ELISA) for toxin A and B and the composite of toxin A and B is presented Table 3 for Day 60/Day 0, Day 180/Day 0, and Day 210/Day 0 in for subjects in the PPSI included in the Day 210 analysis. There were no remarkable differences in the ELISA seroconversion rates for subjects aged 40 to 64 years and subjects aged 65 to 75 years in the FASI in Groups 3, 6, and 7 included in the Day 210 analysis.

The percentage of subjects in the FASI included in the Day 210 analysis who were seropositive for toxin A at baseline and who had a ≥4-fold seroconversion on Day 60 compared to Day 0 was 100% for subjects in Group 3, 92.3% (12/13) of subjects in Group 6, and 87.5% (7/8) of subjects in Group 7. The percentage of subjects in the FASI included in the Day 210 analysis who were seropositive for toxin B at baseline and who had a ≥4-fold seroconversion on Day 60 compared to Day 0 was 94.6% (35/37) of subjects in Group 3, 91.5% (43/47) of subjects in Group 6, and 94.1% (48/51) of subjects in Group 7.

TNA Results—GMTs

For Groups 3 and 7, GMTs for toxin A and B increased from Day 0 through Day 60. For Group 6, the highest GMT was reached at Day 30. In Group 3, the GMTs decreased at Day 210, while in Groups 6 and 7, GMTs increased at Day 210, following a third vaccination at Day 180. This same pattern was seen in subjects aged 40 to 64 years and subjects aged 65 to 75 years. The number of subjects who were seropositive at baseline was higher for toxin B than for toxin A. Seropositivity at baseline enhanced the immune response for toxins A and B at Day 60 in Groups 3 and 7 or Day 30 in Group 6.

For Groups 3 and 7 for subjects in the PPSI included in the Day 210 analysis, GMTs for toxin A (measured by TNA) increased from Day 0 through Day 60, at which point they were 628.6 1/dil and 553.7 1/dil, respectively. For Group 6, the highest GMT before Day 210 was reached at Day 30 (rather than Day 60), at which point it was 158.6 1/dil. In Group 3, the GMTs decreased to 270.2 1/dil at Day 210, while in Groups 6 and 7, GMTs increased markedly to 8939.4 1/dil and 9015.6 1/dil, respectively, at Day 210, following a third vaccination at Day 180. For Groups 3 and 7, GMTs for toxin B (measured by TNA) increased from Day 0 through Day 60, at which point they were 466.3 1/dil and 415.0 1/dil, respectively. For Group 6, the highest GMT before Day 210 was reached at Day 30 (rather than Day 60), at which point it was 351.1 1/dil. In Group 3, the GMTs decreased to 164.4 1/dil at Day 210, while in Groups 6 and 7, GMTs increased to 1488.4 1/dil and 2070.3 1/dil, respectively, at Day 210, following a third vaccination at Day 180.

There were no remarkable differences in TNA GMTs for toxin A or B in subjects aged 40 to 64 years and subjects aged 65 to 75 years in Groups 3, 6, and 7 included in the Day 210 analysis.

For subjects who were seropositive at baseline, baseline GMTs at Day 0 for toxin A were 72.07 1/dil, 44.55 1/dil, and 59.94 1/dil, respectively, and for toxin B were 161.8 1/dil, 79.31 1/dil, and 76.35 1/dil, respectively for subjects in Groups 3, 6, and 7, The GMTs tended to reach peak values many-fold higher at Days 30 or 60 than the GMTs for subjects who were seronegative at baseline.

A TNA bootstrapping ranking analysis was performed for Groups 3, 6, and 7 for subjects in the PPSI included in the Day 210 analysis (Table 4). The probability for Group 3 at Day 60, for toxin A (66.9%), toxin B (58.7%), and the composite of toxin A and B (63.0%), ranked higher than Group 6 or 7.

A summary of the GMFRs (measured by TNA) are presented in Table 5 for subjects in Groups 3, 6, and 7 in the PPSI included in the Day 210 analysis.

For toxin A (measured by TNA) for subjects in the PPSI in the Day 210 analysis, in Group 3, GMFR was highest (31.6) on Day 60 compared to Day 0. In Group 6, GMFR was 8.5 on Day 30 compared to Day 0, 6.1 on Day 60 compared to Day 0, but then reached 419.8 on Day 210 compared to Day 0. In Group 7, GMFR was 26.0 on Day 60 compared to Day 0, but then reached 412.6 on Day 210 compared to Day 0. For toxin B (measured by TNA) for subjects in the PPSI in the Day 210 analysis, in Group 3, GMFR was 14.6 on Day 30 compared to Day 0 and 17.0 on Day 60 compared to Day 0. In Group 6, GMFR was 17.8 on Day 30 compared to Day 0, 13.3 on Day 60 compared to Day 0, and reached 60.2 on Day 210 compared to Day 0. In Group 7, GMFR was 14.2 on Day 30 compared to Day 0, 16.7 on Day 60 compared to Day 0, and reached 70.2 on Day 210 compared to Day 0.

TNA Results—Seroconversion

At Day 60, for toxin A, there was a ≥4-fold rise in seroconversion for 97.0% (64/66) of subjects in Group 3, 41.0% (25/61) of subjects in Group 6, and 82.5% (47/57) of subjects in Group 7. (Subjects in Group 3 and Group 7 received a vaccination at Day 30; the second vaccination for Group 6 was at Day 7.) By contrast, at Day 60, for toxin B, the ≥4-fold rise in seroconversion was similar across treatment groups: 63.6% (42/66) of subjects in Group 3, 57.4% (35/61) of subjects in Group 6, and 63.2% (36/57) of subjects in Group 7. At Day 60, for the composite of toxin A and B, there was a ≥4-fold rise in seroconversion for 62.1% (41/66) of subjects in Group 3, 31.1% (19/61) of subjects in Group 6, and 56.1% (32/57) of subjects in Group 7. A summary of the ≥4-fold seroconversion rates (measured by TNA) for the composite of toxin A and B is presented in Table 6 for Day 60/Day 0, Day 180/Day 0, and Day 210/Day 0 in for subjects in the PPSI included in the Day 210 analysis.

There were no remarkable differences in the TNA seroconversion rates for subjects aged 40 to 64 years and subjects aged 65 to 75 years in the FASI in Groups 3, 6, and 7 included in the Day 210 analysis (Appendix 15, Table 15.56).

The percentage of subjects in the FASI included in the Day 210 analysis who were seropositive for toxin A at baseline and who had a ≥4-fold seroconversion on Day 60 compared to Day 0 was 100% for subjects in Group 3, 96.0% (24/25) of subjects in Group 6, and 100% of subjects in Group 7 (Appendix 15, Table 15.59). The percentage of subjects in the FASI included in the Day 210 analysis who were seropositive for toxin B at baseline and who had a ≥4 fold seroconversion on Day 60 compared to Day 0 was 96.2% (25/26) of subjects in Group 3, 100% of subjects in Groups 6 and 7. The percentage of subjects in the FASI included in the Day 210 analysis who were seronegative for toxin A at baseline and who had a ≥4-fold seroconversion on Day 60 compared to Day 0 was 95.1% (78/82) of subjects in Group 3, 25.0% (17/68) of subjects in Group 6, and 80.0% (60/75) of subjects in Group 7. The percentage of subjects in the FASI included in the Day 210 analysis who were seronegative for toxin B at baseline and who had a ≥4-fold seroconversion on Day 60 compared to Day 0 was 45.6% (31/68) Group 7.

Stage II Conclusion

As in Stage I, the results in Stage II continued to support the safety of the vaccine. No safety signals were identified and the overall tolerability profile was acceptable, and comparable to Stage I. Specifically the number of subjects reporting SAEs was comparable across the groups; there were no SAEs considered related to vaccination. Four subjects died during the study, but the deaths were not considered related to vaccination. Few subjects reported an AE that led to study discontinuation. Solicited reactions (specifically injection site pain and the systemic reaction of myalgia) were somewhat higher in Group 6 and 7 after the last vaccination on Day 180. Biologically significant laboratory parameters were mostly associated with underlying medical conditions.

The vaccine formulation at all 3 schedules was immunogenic for toxin A and B by ELISA and TNA. Immune responses were robust and continued to increase through Day 60 in Groups 3 and 7 and through Day 30 in Group 6. Immune responses in Group 3 remained high at Day 210. There were more subjects who were seropositive at baseline for toxin B than for toxin A. Overall, the schedule Day 0, 7, 30 (Group 3) elicited the best immune response as measured by both ELISA and TNA during the period a subject may be at greatest risk of CDI.

Ultimately, the optimal vaccine schedule should be consistent with a rapid onset of protection during the period of pre-hospitalization, during and after hospitalization, and a high degree of compliance with the regimen. Studies have shown that the highest risk of CDI starts around 3 to 5 days post exposure to hospital spores. Furthermore, it has been shown that 70% of CDI cases occur within 1 month of hospital discharge, with the remainder of cases occurring 3 months after hospital discharge (Premier Database). Globally the mean waiting time for planned surgeries has been estimated to be from 2 weeks to 5 months (31). During the choice of schedule, decision ranking for the Day 60 immune response was given priority, since the Day 60 response should be occurring during the period of greatest CDI risk. While a specific correlate of immunologic protection is not yet known, demonstration of a good immune response at Day 60 and a sustained response through Day 180 were important criteria in the selection of a preferred vaccine regimen that could be expected to provide protection for subjects during and after planned hospitalization.

The vaccine formulation of 100 µg+ALOH was immunogenic for the 3 vaccine injection schedules (Days 0, 7; 30; Days 0, 7, 180; Days 0, 30, 180) tested, at all timepoints, and for both adult (aged 40 to 64 years) and elderly (aged 65 to 75 years) subjects. Immune responses at Days 7 and 14 were similar for the 3 testing schedules in adult and elderly subjects. The ELISA GMCs and TNA GMTs were higher at Days 60 and 180 for subjects in Group 3 than in Group 6 or 7. As expected, subjects in Groups 6 and 7 had the highest GMCs and GMTs at Day 210 because they had been vaccinated 30 days prior on Day 180 (unlike subjects in Group 3). Seroconversion (measured either by ELISA or TNA) was higher on Days 60 and 180 for subjects in Group 3 than in Group 6 or 7. Based on the bootstrap ranking analysis which focused principally on the immune response over the first 60-day period, Group 3 was chosen as the best schedule. Importantly, when viewed over the 180-day period (i.e., Day 0+180 days=Day 180) during which maximum vaccine protection would be desired in patients who have recently entered a defined risk period for CDI, administration of 3 doses with a 0, 7 and 30 day regimen (Group 3) overall provided the best immune response as compared with the other 2 regimens (Groups 6 or 7) taking into consideration the immune responses measured over Days 30, 60 and 180. This period represents a period when patients are likely to be of greatest risk of developing CDI. Overall Group 3 with a vaccine schedule of Days 0, 7, and 30 produced good immune responses at Days 30, 60 and 180. Importantly, the results from Stage II also suggest better compliance of subjects in Group 3, as more of these subjects received all 3 vaccine injections compared to the groups whose third vaccine was at Day 180. It is envisioned that the vaccine would be administered in an out-patient setting, perhaps by a general practitioner or primary care physician, especially those who care for the elderly or those with chronic underlying medical conditions. Because individuals would be immunized in advance of disease onset, by using a Day 0, 7 and 30 vaccine schedule, a protective immune response may best be achieved as early as 1 week after the second vaccine dose (e.g., Day 14). This regimen has also been found to elicit sustained neutralizing Ab titers to both toxins A and B for at least 30 months (e.g., 1000 days), with titres at or above those achieved by day 14, even for seronegative individuals (e.g., naïve individuals). Immune responses have been noted to be durable beyond 30 months for both toxins.

The study also revealed that day zero seropositive individuals exhibited a greater than two- to four-fold increase in seroconversion than seronegative individuals (e.g., naïve individuals) following vaccination. At 14 days post-vaccination (0 and 7 day dosing), seropositive individuals seroconverted (two- and four-fold increase as measured by ELISA or TNA) at a frequency of about two to three times that of seronegative individuals. At 30 days post-vaccination (about 21 days after the second dose and prior to the third dose), seropositive individuals seroconverted (two- and four-fold increase as measured by ELISA) at a higher frequency than seronegative individuals but the difference was not as great. For instance, seroconversion as measured by ELISA (Toxin A and Toxin B) was about 20-30% more frequent in seropositive individuals at day 30. As measured by TNA, seropositive individuals maintained a seroconversion frequency of 2-3 times that of seronegative individuals. It is noted, however, that an increase in antibody titre was demonstrated following each dose for both baseline seropositives and seronegatives.

This regimen has also been found to elicit comparable seroconversion rates (e.g., % of subjects with a 4-fold rise from day 0 as measured by ELISA) for both anti-toxin A and anti-toxin B in adult (aged 40-65 years) and elderly (aged 65-75 years) subjects.

CONCLUSIONS

Results show that the vaccine at the evaluated dose levels is capable of eliciting complete seroconversion to both toxins A and B. Such a response is useful for effectiveness against toxin-A negative/toxin-B positive *C. difficile* pathogenic strains, and against epidemic strains of *C. difficile* that produce greater quantities of toxins A and B. Such a response is also useful in the intended target population, which includes elderly individuals and subjects with diminished immune function. In earlier human clinical studies, a good response was elicited to toxin A but the response to toxin B was less than expected. Results show that the 100 µg dose of antigen increased the seroconversion rate to toxin B above the rates observed with the 50 µg dose. The higher dose of both toxoids A and B was associated with a more rapid response time to seroconversion to both toxins. Priority was given to Day 60 immune responses as this was the time period of greatest CDI risk when subjects were exposed to the hospital setting per epidemiology data. It has been determined that 70% of CDI cases occur within 30 days of discharge from the hospital with the remainder occurring by 3 months after discharge. The vaccine formulation (100 µg+ALOH) chosen after Stage I and evaluated at 3 different schedules (Days 0, 7, 30; Days 0, 7, 180; Days 0, 30, 180) had an acceptable safety profile with no safety signals identified. The vaccine when administered at different schedules induced a strong immune response in adult and elderly subjects as evidenced by GM measurements and seroconversion rates of IgG antibodies and TNA results to toxins A and B. Results show that an immune response could be established by Day 14. The durability of the response at Day 210 was also sustained. Overall, the schedule of Days 0, 7, 30 best met the desired profile of maximum protection during the period of interest through Day 60. In terms of both safety and immunogenicity, the combination of formulation (100 µg+ALOH) and schedule of Days 0, 7, 30 yielded the best results.

While certain embodiments have been described in terms of the preferred embodiments, it is understood that variations and modifications will occur to those skilled in the art. Therefore, it is intended that the appended claims cover all such equivalent variations that come within the scope of the following claims.

TABLE 1

Summary of ELISA GMCs, Groups 1-5 (Per-protocol analysis set for immunogenicity, D 60 analysis)

| Toxin Visit | Group 1 Low dose-adj (Days 0, 7, 30) (N = 70) | | | Group 2 Low dose, no adj (Days 0, 7, 30) (N = 68) | | | Group 3 High dose + adj (Days 0, 7, 30) (N = 73) | | |
|---|---|---|---|---|---|---|---|---|---|
| | M | GMC | (95% CI) | M | GMC | (95% CI) | M | GMC | (95% CI) |
| Toxin A IgG (ELISA - EU/mL) | | | | | | | | | |
| Day 0, V01 | 70 | 0.82 | (0.76; 0.88) | 68 | 0.90 | (0.78; 1.03) | 73 | 0.92 | (0.80; 1.06) |
| Day 14, V03 | 69 | 5.17 | (2.91; 9.21) | 68 | 3.90 | (2.07; 7.36) | 72 | 4.18 | (2.34; 7,46) |
| Day 30, V04 | 70 | 24.37 | (14.86; 39.97) | 68 | 9.49 | (5.42; 16.62) | 72 | 17.30 | (10.52; 28.43) |
| Day 60, V05 | 69 | 76.65 | (51.80; 113.42) | 68 | 59.66 | (41.09; 86.61) | 73 | 91.53 | (63.30; 132.36) |
| Toxin B IgG (ELISA - EU/mL) | | | | | | | | | |
| Day 0, V01 | 70 | 0.97 | (0.71; 1.31) | 68 | 0.97 | (0.68; 1.39) | 73 | 1.32 | (0.88; 1.98) |
| Day 14, V03 | 70 | 20.34 | (8.68; 47.64) | 68 | 8.88 | (3.74; 21.06) | 73 | 19.95 | (8.59; 46.35) |
| Day 30, V04 | 70 | 47.94 | (22.14; 103.81) | 68 | 18.65 | (8.23; 42.25) | 73 | 50.66 | (22.49; 114.09) |
| Day 60, V05 | 70 | 80.93 | (44.95; 145.70) | 68 | 77.90 | (39.96; 151.85) | 73 | 125.3 | (71.1; 221.0) |

| Toxin Visit | Group 4 High dose, no adj (Days 0, 7, 30) (N = 73) | | | Group 5 Placebo (Days 0, 7, 30) (N = 38) | | |
|---|---|---|---|---|---|---|
| | M | GMC | (95% CI) | M | GMC | (95% CI) |
| Toxin A IgG (ELISA - EU/mL) | | | | | | |
| Day 0, V01 | 71 | 0.98 | (0.83; 1.15) | 38 | 0.88 | (0.76; 1.02) |
| Day 14, V03 | 73 | 5.16 | (2.76; 9.65) | 38 | 0.93 | (0.79; 1.09) |
| Day 30, V04 | 73 | 16.52 | (9.02; 30.27) | 38 | 1.19 | (0.80; 1.77) |
| Day 60, V05 | 73 | 83.12 | (49.48; 139.66) | 38 | 1.53 | (0.89; 2.62) |
| Toxin B IgG (ELISA - EU/mL) | | | | | | |
| Day 0, V01 | 73 | 1.61 | (1.09; 2.38) | 38 | 0.99 | (0.65; 1.52) |
| Day 14, V03 | 73 | 27.58 | (11.48; 66.29) | 38 | 1.05 | (0.66; 1.66) |
| Day 30, V04 | 73 | 53.12 | (22.24; 126.87) | 38 | 1.30 | (0.71; 2.35) |
| Day 60, V05 | 73 | 156.8 | (84.2; 292.2) | 38 | 1.62 | (0.79; 3.29) |

N: number of subjects analyzed according to the per-protocol analysis set for immunogenicity
M: number of subjects available for the endpoint
The 2-sided 95% CI of a geometric mean is based on the Student t-distribution.

TABLE 2

Summary of seroconversion rates for the unselected groups (Full analyses set for immunogenicity, D 210 analysis)

| | | Visit | Group 1 Low dose + adj (Days 0, 7, 30) (N = 94) | | | Group 2 Low dose, no adj (Days 0, 7, 30) (N = 98) | | |
|---|---|---|---|---|---|---|---|---|
| | | | n/M | % | (95% CI) | n/M | % | (95% CI) |
| ELISA Composite Toxin A and B IgG | ≥4 fold rise | Day 60/Day 0 | 75/87 | 86.2 | (77.2; 92.7) | 70/94 | 74.5 | (64.4; 82.9) |
| | | Day 180/Day 0 | 56/79 | 70.9 | (59.6; 80.6) | 44/81 | 54.3 | (42.9; 65.4) |
| | | Day 210/Day 0 | 51/74 | 68.9 | (57.1; 79.2) | 36/76 | 47.4 | (35.8; 59.2) |
| TNA Composite Toxin A and B | ≥4 fold rise | Day 60/Day 0 | 49/88 | 55.7 | (44.7; 66.3) | 47/94 | 50.0 | (39.5; 60.5) |
| | | Day 180/Day 0 | 36/79 | 45.6 | (34.3; 57.2) | 32/81 | 39.5 | (28.8; 51.0) |
| | | Day 210/Day 0 | 29/73 | 39.7 | (28.5; 51.9) | 31/76 | 40.8 | (29.7; 52.7) |

TABLE 2-continued

Summary of seroconversion rates for the unselected groups
(Full analyses set for immunogenicity, D 210 analysis)

|  |  | Group 4 High dose, no adj (Day 0, 7, 30) (N = 96) | | | Group 5 Placebo (Days 0, 7, 30) (N = 48) | | |
|---|---|---|---|---|---|---|---|
|  |  | n/M | % | (95% CI) | n/M | % | (95% CI) |
| ELISA Composite | ≥4 fold rise | 75/88 | 85.2 | (76.1; 91.9) | 3/48 | 6.3 | (1.3; 17.2) |
| Toxin A and B IgG |  | 55/85 | 64.7 | (53.6; 74.8) | 1/41 | 2.4 | (0.1; 12.9) |
|  |  | 48/74 | 64.9 | (52.9; 75.6) | 1/37 | 2.7 | (0.1; 14.2) |
| TNA Composite | ≥4 fold rise | 56/90 | 62.2 | (51.4; 72.2) | 0/48 | 0.0 | (0.0; 7.4) |
| Toxin A and B |  | 48/86 | 55.8 | (44.7; 66.5) | 0/41 | 0.0 | (0.0; 8.6) |
|  |  | 43/74 | 58.1 | (46.1; 69.5) | 0/37 | 0.0 | (0.0; 9.5) |

N: number of subjects analyzed according to the full analysis set for immunogenicity.
M: number of subjects available for the endpoint.
Seroconversion is defined as a minimum 4 fold increase from the indicated visit.
Exact 2-sided 95% CI for the single proportion is based on the Clopper-Pearson method.

TABLE 3

Summary of ELISA serconversion rates, Groups 3, 6 and 7 (per-protocol analysis set for immunogenicity, Day 210 analysis)

| Toxin | Visit |  | Group 3 High dose + adj (Days 0, 7, 30) (N = 66) | | | Group 6 High dose + adj (Days 0, 7, 180) (N = 61) | | | Group 7 High dose + adj (Days 0, 30, 180) (N = 57) | | |
|---|---|---|---|---|---|---|---|---|---|---|---|
|  |  |  | n/M | % | (95% CI) | n/M | % | 95% CI | n/M | % | (95% CI) |
| Toxin A IgG | Day 60/Day 0 | ≥4-fold rise | 64/66 | 97.0 | (89.5; 99.6) | 40/61 | 65.6 | (52.3; 77.3) | 52/57 | 91.2 | (80.7; 97.1) |
|  | Day 180/Day 0 | ≥4-fold rise | 56/66 | 84.8 | (73.9; 92.5) | 31/61 | 50.8 | (37.7; 63.9) | 41/57 | 71.9 | (58.5; 83.0) |
|  | Day 210/Day 0 | ≥4-fold rise | 54/66 | 81.8 | (70.4; 90.2) | 61/61 | 100.0 | (94.1; 100.0) | 57/57 | 100.0 | (93.7; 100.0) |
| Toxin B IgG | Day 60/Day 0 | ≥4-fold rise | 61/66 | 92.4 | (83.2; 97.5) | 52/61 | 85.2 | (73.8; 93.0) | 51/57 | 89.5 | (78.5; 96.0) |
|  | Day 180/Day 0 | ≥4-fold rise | 49/66 | 74.2 | (62.0; 84.2) | 38/61 | 62.3 | (49.0; 74.4) | 41/57 | 71.9 | (58.5; 83.0) |
|  | Day 210/Day 0 | ≥4-fold rise | 46/66 | 69.7 | (57.2; 80.4) | 57/61 | 93.4 | (84.1; 98.2) | 53/57 | 93.0 | (83.0; 98.1) |
| Composite | Day 60/Day 0 | ≥4-fold rise | 60/66 | 90.9 | (81.3; 96.6) | 37/61 | 60.7 | (47.3; 72.9) | 48/57 | 84.2 | (72.1; 92.5) |
|  | Day 180/Day 0 | ≥4-fold rise | 45/66 | 68.2 | (55.6; 79.1) | 23/61 | 37.7 | (25.6; 51.0) | 31/57 | 54.4 | (40.7; 67.6) |
|  | Day 210/Day 0 | ≥4-fold rise | 41/66 | 62.1 | (49.3; 73.8) | 57/61 | 93.4 | (84.1; 98.2) | 53/57 | 93.0 | (83.0; 98.1) |

N: number of subjects analyzed according to the full analysis set for immunogenicity.
M: number of subjects available for the endpoint.
Composite: when a subject reaches the indicated seroconversion for both toxins simultaneously.
Exact 2-sided 95% CI for the single proportion is based on the Clopper-Pearson method. 2-sided 95% CI for the difference of proportions is based on the Newcombe-Wilson score method.

TABLE 4

TNA ranking analysis for Groups 3, 6 and 7 (per-protocol analysis set for immunogenicity, Day 210 analysis)

| Toxin | Time point | Treatment group | Probability |
|---|---|---|---|
| Toxin A (TNA - l/dil) | Day 60 | Group 3 | 66.9 |
|  |  | Group 7 | 33.1 |
|  |  | Group 6 | 0.0 |
|  | Day 14 | Group 6 | 52.9 |
|  |  | Group 7 | 44.3 |
|  |  | Group 3 | 2.8 |
|  | Day 210 | Group 7 | 55.6 |
|  |  | Group 6 | 44.4 |
|  |  | Group 3 | 0.0 |
| Toxin B (TNA - l/dil) | Day 60 | Group 3 | 58.7 |
|  |  | Group 7 | 37.6 |
|  |  | Group 6 | 3.7 |
|  | Day 14 | Group 7 | 51.5 |
|  |  | Group 6 | 31.9 |
|  |  | Group 3 | 16.6 |
|  | Day 210 | Group 7 | 83.3 |
|  |  | Group 6 | 16.7 |
|  |  | Group 3 | 0.0 |
| Composite | Day 60 | Group 3 | 63.0 |
|  |  | Group 7 | 36.6 |
|  |  | Group 6 | 0.4 |
|  | Day 14 | Group 7 | 53.1 |
|  |  | Group 6 | 40.7 |
|  |  | Group 3 | 6.2 |
|  | Day 210 | Group 7 | 69.5 |
|  |  | Group 6 | 30.6 |
|  |  | Group 3 | 0.0 |

TABLE 5

| | | Group 3 High dose + adj (Days 0, 7, 30) (N = 66) | | | Group 6 High dose + adj (Days 0, 7, 180) (N = 61) | | | Group 7 High dose + adj (Days 0, 30, 180) (N = 57) | | |
|---|---|---|---|---|---|---|---|---|---|---|
| Toxin | Visit | M | GMFR | (95% CI) | M | GMFR | (95% CI) | M | GMFR | (95% CI) |
| Toxin A | Day 7/Day 0 | 66 | 1.7 | (1.2; 2.4) | 61 | 1.6 | (1.1; 2.2) | 57 | 1.7 | (1.2; 2.6) |
| | Day 14/Day 0 | 66 | 4.5 | (2.6; 8.0) | 61 | 6.2 | (3.3; 11.5) | 57 | 5.6 | (3.2; 9.9) |
| | Day 14/Day 7 | 66 | 2.7 | (1.9; 3.9) | 61 | 3.9 | (2.4; 6.2) | 57 | 3.2 | (2.2; 4.5) |
| | Day 30/Day 0 | 66 | 5.7 | (3.5; 9.3) | 61 | 8.5 | (5.0; 14.7) | 57 | 4.4 | (2.6; 7.3) |
| | Day 30/Day 7 | 66 | 3.4 | (2.4; 4.8) | 61 | 5.4 | (3.5; 8.3) | 57 | 2.5 | (1.8; 3.4) |
| | Day 30/Day 14 | 66 | 1.2 | (1.0; 1.6) | 61 | 1.4 | (1.1; 1.8) | 57 | 0.7 | (0.6; 0.9) |
| | Day 60/Day 0 | 66 | 31.6 | (22.8; 43.7) | 61 | 6.1 | (3.8; 9.7) | 57 | 26.0 | (16.5; 40.8) |
| | Day 60/Day 30 | 66 | 5.6 | (4.0; 7.7) | 61 | 0.7 | (0.6; 0.8) | 57 | 5.9 | (4.1; 8.6) |
| | Day 180/Day 0 | 65 | 14.6 | (11.2; 19.1) | 61 | 4.7 | (3.2; 6.9) | 57 | 11.3 | (7.5; 17.2) |
| | Day 210/Day 0 | 66 | 13.6 | (10.5; 17.6) | 61 | 419.8 | (284.7; 619.0) | 57 | 412.6 | (284.3; 598.7) |
| Toxin B | Day 7/Day 0 | 66 | 1.8 | (1.3; 2.4) | 61 | 2.4 | (1.7; 3.4) | 57 | 2.2 | (1.6; 3.2) |
| | Day 14/Day 0 | 66 | 11.9 | (6.2; 22.7) | 61 | 16.3 | (8.1; 33.0) | 57 | 16.3 | (7.9; 33.3) |
| | Day 14/Day 7 | 66 | 6.7 | (4.0; 11.0) | 61 | 6.8 | (4.1; 11.3) | 57 | 7.2 | (4.1; 12.5) |
| | Day 30/Day 0 | 66 | 14.6 | (7.7; 27.6) | 61 | 17.8 | (8.9; 35.5) | 57 | 14.2 | (7.3; 27.8) |
| | Day 30/Day 7 | 66 | 8.2 | (4.7; 14.0) | 61 | 7.4 | (4.4; 12.4) | 57 | 6.3 | (3.7; 10.8) |
| | Day 30/Day 14 | 66 | 1.2 | (0.9; 1.6) | 61 | 1.1 | (0.9; 1.3) | 57 | 0.9 | (0.8; 1.0) |
| | Day 60/Day 0 | 66 | 17.0 | (9.7; 29.7) | 61 | 13.3 | (7.1; 24.7) | 57 | 16.7 | (9.0; 30.8) |
| | Day 60/Day 30 | 66 | 1.2 | (1.0; 1.4) | 61 | 0.7 | (0.7; 0.8) | 57 | 1.2 | (1.0; 1.4) |
| | Day 180/0ay 0 | 66 | 6.8 | (4.3; 10.8) | 61 | 8.6 | (5.1; 14.4) | 57 | 9.0 | (5.4; 14.7) |
| | Day 210/Day 0 | 66 | 6.4 | (4.1; 10.0) | 61 | 60.2 | (35.4; 102.2) | 57 | 70.2 | (43.0; 114.7) |

N: number of subjects analyzed according to the full analysis set for immunogenicity.
M: number of subjects available for the endpoint.
The 2-sided 95% CI of a GMFR is based on the Student t-distribution.

TABLE 6

Summary of TNA seroconversion rates, Groups 3, 6 and 7 (per-protocol analysis set for immunogenicity, Day 210 analysis)

| | | | Group 3 High dose + adj (Days 0, 7, 30) (N = 66) | | | Group 6 High dose + adj (Days 0, 7, 180) (N = 61) | | | Group 7 High dose + adj (Days 0, 30, 180) (N = 57) | | |
|---|---|---|---|---|---|---|---|---|---|---|---|
| Toxin | Visit | | n/M | % | (95% CI) | n/M | % | (95% CI) | n/M | % | (95% CI) |
| Toxin A | Day 60/Day 0 | ≥4-fold rise | 64/66 | 97.0 | (89.5; 99.6) | 25/61 | 41.0 | (28.6; 54.3) | 47/57 | 82.5 | (70.1; 91.3) |
| (TNA - l/dil) | Day 180/Day 0 | ≥4-fold rise | 60/65 | 92.3 | (83.0; 97.5) | 27/61 | 44.3 | (31.6; 57.6) | 42/57 | 73.7 | (60.3; 84.5) |
| | Day 210/Day 0 | ≥4-fold rise | 58/66 | 87.9 | (77.5; 94.6) | 61/61 | 100.0 | (94.1; 100.0) | 57/57 | 100.0 | (93.7; 100.0) |
| Toxin B | Day 60/Day 0 | ≥4-fold rise | 42/66 | 63.6 | (50.9; 75.1) | 35/61 | 57.4 | (44.1; 70.0) | 36/57 | 63.2 | (49.3; 75.6) |
| (TNA - l/dil) | Day 180/Day 0 | ≥4-fold rise | 35/66 | 53.0 | (40.3; 65.4) | 33/61 | 54.1 | (40.9; 66.9) | 34/57 | 59.6 | (45.8; 72.4) |
| | Day 210/Day 0 | ≥4-fold rise | 34/66 | 51.5 | (38.9; 64.0) | 53/61 | 86.9 | (75.8; 94.2) | 51/57 | 89.5 | (78.5; 96.0) |
| Composite | Day 60/Day 0 | ≥4-fold rise | 41/66 | 62.1 | (49.3; 73.8) | 19/61 | 31.1 | (19.9; 44.3) | 32/57 | 56.1 | (42.4; 69.3) |
| | Day 180/Day 0 | ≥4-fold rise | 33/65 | 50.8 | (38.1; 63.4) | 21/61 | 34.4 | (22.7; 47.7) | 27/57 | 47.4 | (34.0; 61.0) |
| | Day 210/Day 0 | ≥4-fold rise | 31/66 | 47.0 | (34.6; 59.7) | 53/61 | 86.9 | (75.8; 94.2) | 51/57 | 89.5 | (78.5; 96.0) |

N: number of subjects analyzed according to the full analysis set for immunogenicity.
M: number of subjects available for the endpoint.
Composite: when a subject reaches the indicated seroconversion for both toxins simultaneously.
Exact 2-sided 95% CI for the single proportion is based on the Clopper-Pearson method. 2-sided 95% CI for the difference of proportions is based on the Newcombe-Wilson score method.

The invention claimed is:

1. A method for eliciting an immune response against *C. difficile* toxin A and toxin B in an adult human subject at risk for a primary symptomatic *C. difficile* infection, the method comprising administering to the subject a composition comprising *C. difficile* toxoid A and toxoid B at a purity of about 90% or higher (w/w) at least three times, the first and second administrations being at least about seven days apart.

2. The method of claim 1 wherein the immune response elicited is sufficient to prevent and/or reduce a primary symptomatic *C. difficile* infection in the adult human subject.

3. The method of claim 1 wherein the immune response elicited is sufficient to prevent the onset of a symptomatic *C. difficile* infection in the adult human subject.

4. The method of claim 1 wherein the second administration is about 7 days after the first administration and the third administration is about 30 days after the first or second administration.

5. The method of claim 4 wherein the third administration is about 30 days after the first administration.

6. The method of claim 1 wherein the second administration is about 7 days after the first administration and the third administration is about 180 days after the first or second administration.

7. The method of claim 6 wherein the third administration is about 180 days after the first administration.

8. The method of claim 1 wherein the composition comprises each of *C. difficile* toxoid A and toxoid B, having a purity of at least about 90% or greater, in a ratio of about 3:1 to about 1:1.

9. The method of claim 8 wherein the ratio of *C. difficile* toxoid A and toxoid B is about 3:2.

10. The method of claim 1 wherein the composition comprises a combined total of *C. difficile* toxoid A and toxoid B of about 40 to 500 µg.

11. The method of claim 1 wherein the composition comprises an adjuvant.

12. The method of claim 11 wherein the composition comprises an aluminum adjuvant.

13. The method of claim 1 wherein the subject at risk is at least 40 years of age and:
   (i) has had, in the 12 month period before the first administration, at least 2 hospital stays, each lasting at least about 24 or 72 hours, and has received systemic but not topical antibiotics, or
   (ii) is anticipated to have an in-patient hospitalization for a planned surgical procedure within 60 days of the first administration.

14. The method of claim 13, wherein the anticipated hospitalization is planned to be for at least about 24 or 72 hours and is for a surgery involving at least one of the following systems:
   (i) kidney/bladder/urinary system;
   (ii) musculoskeletal system;
   (iii) respiratory system;
   (iv) circulatory system; and
   (v) central nervous system.

15. The method of claim 1 wherein the adult human subject is at least about 65 years or older.

16. The method of claim 15 wherein an immune response against *C. difficile* toxin A and/or toxin B is sustained for at least about 60 days.

17. The method of claim 16 wherein an immune response against *C. difficile* toxin A and/or toxin B is sustained for at least about 210 days.

18. The method of claim 17 wherein an immune response against *C. difficile* toxin A and/or toxin B is sustained for at least about 1000 days.

19. A composition comprising *C. difficile* toxoid A and toxoid B at a purity of about 90% or higher (w/w) for use in a method for eliciting an immune response against *C. difficile* toxin A and toxin B in a human subject, the method comprising administering the the subject the composition at least three times, the first and second administrations being at least about 7 days apart.

20. The method of claim 1 wherein the first and second administrations are seven days apart.

21. A method for eliciting an immune response against *C. difficile* toxin A and toxin B in an adult human subject at risk for a primary symptomatic *C. difficile* infection, the method comprising administering to the subject a composition comprising *C. difficile* toxoid A and toxoid B and an aluminum adjuvant at least three times, wherein the second administration is about 7 days after the first administration and the third administration is about 180 days after the first or second administration.

22. A method for eliciting an immune response against *C. difficile* toxin A and toxin B in an adult human subject at risk for a primary symptomatic *C. difficile* infection, the method comprising administering to the subject a composition comprising *C. difficile* toxoid A and toxoid B and an aluminum adjuvant at least three times, wherein the third administration is about 180 days after the first administration.

* * * * *